US006689362B1

(12) United States Patent
Uckun

(10) Patent No.: US 6,689,362 B1
(45) Date of Patent: Feb. 10, 2004

(54) METHOD FOR TREATING T-LINEAGE LEUKEMIAS AND LYMPHOMAS USING A CD7-SPECIFIC MONOCLONAL ANTIBODY (TXU-7) LINKED TO THE POKEWEED ANTIVIRAL PROTEIN (PAP)

(75) Inventor: Fatih M. Uckun, White Bear Lake, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 0 days.

(21) Appl. No.: 09/453,641

(22) Filed: Dec. 3, 1999

Related U.S. Application Data

(63) Continuation-in-part of application No. 09/014,028, filed on Jan. 27, 1998, now Pat. No. 6,372,217.
(60) Provisional application No. 60/048,364, filed on Jun. 3, 1997.

(51) Int. Cl.[7] ............................................. A61K 39/395

(52) U.S. Cl. ............................... 424/155.1; 424/154.1; 530/388.75; 530/388.8

(58) Field of Search ........................... 435/5; 424/154.1, 424/155.1; 530/388.75, 388.8

(56) References Cited

U.S. PATENT DOCUMENTS

| | | | | |
|---|---|---|---|---|
| 4,401,592 A | * | 8/1983 | Yoshikumi et al. | 260/112 |
| 4,675,386 A | | 6/1987 | Royston et al. | 530/387 |
| 4,831,117 A | | 5/1989 | Uckun | 530/387 |

FOREIGN PATENT DOCUMENTS

| | | | | |
|---|---|---|---|---|
| WO | WO96/05865 | 2/1996 | ......... | A61K/47/48 |
| WO | WO97/25071 | 7/1997 | ......... | A61K/47/48 |

OTHER PUBLICATIONS

Hertler, A. and A. Frankel, 1989, "Immunotoxins: a clinical review of their use in the treatment of malignancies", J. Clin. Oncol. 7(12):1932–1942.*
Ren, E. C., 1990, "Immunotoxins: the potential in cancer treatment", Annal. Acad. Med. 19(2):240–243.*
Dillman, R. O., 1989, "Monoclonal antibodies for treating cancer", Annal. Intern. Med. 111:592–603.*
Ilercil, O., et al., 1994, "Neurotoxicity of immunotoxins", Molec. Chem. Neuropath. 21:379–386.*
Allan, J.S., "Human Immunodeficency Virus–Related Infectios in Animal Model Systems", AIDS: Biology, Diagnosis, Treatment, and Prevention, 4th ed., DeVita, Sr., V.T., et al., eds., Lippincott–Raven Publishers, pp. 15–27, (1997).
Carayannopoulos, L., et al., "Immunoglobulins—Structure and Function", Fundamental Immunology, 3rd ed., W.E. Paul, ed., Raven Press, Ltd., NY, pp. 286–304, (1993).

Gunther, R., et al., "In Vivo Anti–Leukemic Efficacy of Anti–CD7–Pokeweed Antiviral Protein Immunotoxin Against Human T–Lineage Acute Lymphoblastic Leukemia/Lymphoma in Mice with Severe Combined Immunodeficiency", Leukemia, 7 (2), pp. 298–309, (Feb. 1993).
Hirsch, M.S., et al., "Antiretroviral Therapy", AIDS: Biology, Diagnosis, Treatment, and Prevention, 4th ed., DeVita, Sr., V.T., et al., eds., Lippincott–Raven Publishers, pp. 495–508, (1997).
Lambert, J., et al., "Purified Immunotoxins that are Reactive with Human Lymphoid Cells", J. Biological Chemistry, 260 (22), pp. 12035–12041, (Oct. 5, 1985).
Lee, T., "Acquired Immunodefiency Disease Vaccines: Design and Development", AIDS: Biology, Diagnosis, Treatment, and Prevention, 4th ed., DeVita, Sr., V.T., et, al., eds., Lippincott–Raven Publishers, pp. 605–616, (1997).
Lewis, A.D., et al., "Development Animal Models for AIDS research–progress and problems", TIBTECH, 13, pp. 142–150, (1995).
Myers, D.E., et al., "Large Scale Manufacturing of TXU(Anti–CD7)–Pokeweed Antiviral Protein (PAP) Immunoconjugate for Clinical Trials", Leukemia and Lymphoma, 27, pp. 275–302, (1997).
Pincus, S.H., "Therapeutic potential of anti–HIV immunotoxins", Antivir. Res., 33, pp. 1–9, (1996).
Ramachandran, R.V., et al., "Failure of Short–Term CD4–PE40 infusions to reduce virus load in human immunodeficiency virus–infected persons", J. Infect. Dis., 170, pp. 1009–1013, (Oct. 1994).

(List continued on next page.)

Primary Examiner—Laurie Scheiner
Assistant Examiner—Jeffrey S. Parkin
(74) Attorney, Agent, or Firm—Schwegman, Lundberg, Woessner & Kluth, P.A.

(57) ABSTRACT

Acute lymphoblastic leukemia (ALL) and acute myeloid leukemia (AML) are common leukemias in both children and adults. Current treatment strategies are inadequate and often result in patient toxicity and relapse. Accordingly, the need exists for a T-cell-specific immunotoxin with sufficient stability and efficacy to eliminate cell populations associated with various T-cell malignancies. The present invention addresses this concern by providing a biotherapeutic agent (e.g., an immunoconjugate or immunotoxin) comprising a monoclonal antibody (MoAb TXU-7) specific to mammalian T-cell/myeloid antigen CD7 linked to the pokeweed antiviral protein (PAP). The CD7 antigen is expressed on human T-lineage lymphoid cells and leukemic progenitor cells in T-lineage lymphoid malignancies. PAP is a member of the hemitoxin group of toxins and inactivates ribosomes by the removal of a single adenosine from the conserved loop sequence found near the 3' terminus of all larger RNAs. This specific depurination abrogates the ability of elongation factors to interact with ribosomes and results in irreversible shut-down of protein synthesis. The PAP toxin was linked to the TXU-7 Mab to produce a TXU-7-PAP immunoconjugate. This immunotoxin is stable in vivo and effective in killing and eliminating CD7-expressing T-lineage leukemic cells.

14 Claims, 9 Drawing Sheets

OTHER PUBLICATIONS

Uckun, F.M., et al., "TXU(Anti–CD7)—Pokeweed Antiviral Protein as a Potent Inhibitor of Human Immunodeficiency Virus", *Antimicrobial Agents and Chemotherapy, 42* (2), pp. 383–388, (Feb. 1998).

Vitetta, et al., "Immunotoxins: Magic Bullets or Misguided Missiles", *Trends Pharmacol. Sci. 14*, pp. 148–154, (1993).

Waurzyniak, B., et al., "In Vivo Toxicity, Pharmacokinetics, and Antileukemic Activity of TXU (Anti–CD7)–Pokeweed Antiviral Protein Immunotoxin", *Clinical Cancer Research, 3*, pp. 881–890, (Jun. 1997).

Zarling, J.M., et al., "Inhibition of HIV replication by pokeweed antiviral protein targeted to CD4+ cells by monoclonal antibodies", *Nature, 347*, pp. 92–95, (Sep. 6, 1990).

Zarling, J.M., et al., "Inhibition of HIV–1 replication in seropositive patients' CD4+ T–cells by pokeweed antiviral protein–monoclonal antibody conjugates",*Int. J. Immunopharmac., 13* (*Suppl. 1*), pp. 63–68, (1991).

Carayannopoulos, L., et al., "Immunoglobulins—Structure and Function", *Fundamental Immunology, 3rd ed., W.E. Paul, ed., Raven Press, Ltd., NY*, 286–304, (1993).

Lambert, J., et al., "Purified Immunotoxins that are Reactive with Human Lymphoid Cells", *J. Biological Chemistry, 260* (22), pp. 12035–12041, (Oct. 5, 1985).

Myers, D.E., et al., "Large Scale Manufacturing of TXU(Anti–CD7)–Pokeweed Antiviral Protein (PAP) Immunoconjugate for Clinical Trials", *Leukemia and Lymphoma, 27*, pp. 275–302, (1997).

Vitetta, et al., "Immunotoxins: Magic Bullets or Misguided Missiles", *Trends Pharmacol. Sci. 14*, 148–154, (1993).

Waurzyniak, B., et al., "In Vivo Toxicity, Pharmacokinetics, and Antileukemic Activity of TXU (Anti–CD7)–Pokeweed Antiviral Protein Immunotoxin", *Clinical Cancer Research*, vol. 3, pp. 881–890, (Jun. 1997).

\* cited by examiner

Peritoneal Cavity Cells

Spleen Cells

Peritoneal Cavity Cells

METHOD FOR TREATING T-LINEAGE LEUKEMIAS AND LYMPHOMAS USING A CD7-SPECIFIC MONOCLONAL ANTIBODY (TXU-7) LINKED TO THE POKEWEED ANTIVIRAL PROTEIN (PAP)

CROSS REFERENCE TO RELATED APPLICATIONS

This application is a continuation-in-part application of U.S. application Ser. No. 09/014,028, filed Jan. 27, 1998, now U.S. Pat. No. 6,372,217, which is a continuation-in-part application of U.S. provisional application Ser. No. 60/048,364, filed Jun. 3, 1997, the disclosures of which are incorporated by reference herein.

The invention described herein was made with government support under Grant Number CA13539 and CA21737, awarded by the National Institutes of Health. The United States Government has certain rights in the invention.

BACKGROUND OF THE INVENTION

Acute lymphoblastic leukemia (ALL) is the most common form of childhood malignancy. Champlin et al., *Blood*, 73, 2051 (1989). Each year about 1250 children less than 15 years of age are found to have acute lymphoblastic leukemia. Champlin et al., cited supra. Recently, dramatic improvements in the multiagent chemotherapy of children with ALL have resulted in cure rates of 70–75%. Poplack et al., *Pediatric Clinics of North America*, 35, 903 (1988). However, despite these recent improvements, as many as 1 in 5 patients will eventually suffer leukemic relapse. Riehm et al., *Haematol. Blood Transf.*, 33, 439 (1990). This occurrence of relapsed patients equates to 250 cases/year and is equivalent to the number of newly diagnosed cases of childhood acute nonlymphoblastic leukemia, medulloblastoma, and rhabxomyosarcoma Furthermore, this relapse rate surpasses the number of newly diagnosed cases of childhood Ewings sarcoma, osteogenic sarcoma, hepatoma, and germ cell tumors. The unsatisfactory outcome of this population makes a significant contribution to overall pediatric cancer mortality, despite the excellent outcome for the substantial majority of children with ALL.

Currently, the major challenge in the treatment of childhood ALL is to cure patients who have relapsed despite intensive multiagent chemotherapy. Champlin et al., cited supra. For patients who have relapsed while on therapy or shortly after elective cessation of therapy, the overall survival is very poor. Poplack et al., cited supra. Treatment of these relapsed children has generally employed either intensive chemotherapy to achieve a second remission, subsequent use of either nonablative chemotherapy or ablative radiochemotherapy and bone marrow transplantation (BMT). Kersey et al., *N Engl. J. Med.*, 117, 461 (1987). However, recurrence of leukemia is the major obstacle to the success of either approach. Dicke et al., *Clin. Hematol.*, 15, 86 (1986).

Furthermore, treatment of these relapsed patients by the intensification of cytotoxic therapy using conventional drugs-will likely cause overlapping toxicities and may result in delays which may erode the intensity of therapy. Consequently, the development of new potent anti-ALL drugs and the design of combinative treatment protocols utilizing these new agents, have emerged as focal points for research in the therapy of relapsed ALL.

Acute myeloid leukemia (AML) is the most common form of acute leukemia in adults and the second most frequent leukemia in children, accounting for 20–25% of acute childhood leukemias. Priesier et al., *Blood*, 80, 2600 (1992). Though the majority of patients with myeloid leukemias initially respond to intensive chemotherapy regimens, most will relapse and eventually succumb to their disease. Additionally, attempts to identify useful and specific prognostic factors to effectively stratify good and poor outcome AML patients have generally not been successful, with the result that all patients receive very intensive therapy at the price of great morbidity. Furthermore, contemporary multiagent chemotherapy regimens for AML fail to cure more than half of the patients because of multidrug resistance of leukemia cells and often lead to potentially fatal systemic toxicity. Gale et al., *Sem. Hematol.*, 24, 40 (1987).

Finally, although allogeneic bone marrow transplantation has been demonstrated to be an effective therapy for many patients with myeloid leukemia, its application is limited by the availability of suitable HLA-matched and MLC-unreactive donors. Woods et al., *J. Clin. Oncol.*, 11, 1448 (1993). In autologous bone marrow transplantation for childhood AML, gene marker studies have indicated that subclinical disease in unpurged "remission" marrow harvested for transplantation contributes significantly to disease recurrence. Brenner et al., *Lancet*, 341, 85 (1993). Myeloablative chemotherapy or supralethal radiochemotherapy followed by allogeneic or autologous bone marrow transplantation are associated with considerable morbidity and mortality and fail to substantially improve the overall survival of AML patents, underscoring the need for rational, drug design-based therapies for AML. Yeaper et al., *New Engl. J. Med.*, 315, 141 (1986); Woods et al., cited supra.

Another disease of the immune system is acquired immunodeficiency syndrome (AIDS). Infection with the human immunodeficiency virus type I (HIV-1) constitutes a worldwide public health problem. Venkatesan, *Science*, 241, 1481 (1988). The critical basis for the immunopathogenesis of HIV infection is the depletion of the CD4+ helper/inducer subset of T-cells, resulting in profound immunosuppression. See Dahlgleish et al, *Nature*, 312, 763 (1984); Fauci, *Clin. Res.*, 32, 491 (1985); Ho et al., *N. Engl. J. Med.*, 317, 278 (1987). HIV has a selective tropism for CD4+ T-cells and macrophages which is mediated by interaction of its envelope (env) protein gp 120 with an essential component of the cell surface receptor for HIV-1, the CD4 antigen. Lasky et al., *Science*, 233 209 (1986). After HIV binds to the first domain of the CD4 molecule via the external envelope glycoprotein gp120, the virus is internalized and uncoated. Fauci, *Science*, 239, 617(1988). Once uncoated, the viral genomic RNA is transcribed to DNA by the enzyme reverse transcriptase. The proviral DNA is then integrated into the host chromosomal DNA. After integration of the provirus, the infection may assume a latent phase or the proviral DNA may transcribe viral genomic RNA and messenger RNA. Protein synthesis, processing, and virus assembly occur with budding of the mature virion from the cell surface.

At present, AIDS is incurable and treatment modalities that reduce HIV-1 replication in vivo by using reverse transcriptase inhibitors such as zidovudine/ZDV (formerly termed azidothymidine/AZT) and dideoxyinosine (ddI) cause substantial side effects. Yarchoan et al., *Blood*, 78, 859 (1991). Although ZDV delays the disease progression in HIV-1 seropositive asymptomatic individuals and has improved the survival of patients with AIDS and AIDS-related complex (ARC), the therapeutic response is frequently transient. Volberding et al., *N. Engl. J. Med.*, 322, 941 (1990); Fischl et al., *Ann. Intern. Med.*, 112, 727 (1990); Fischl et al., *N. Engl. J. Med.*, 317, 185 (1987). Moreover, variants of HIV-1 that are resistant to ZDV emerge to thwart the success of continued therapy. Erice et al., *Clinical Infectious Disease*, 18, 149 (1994). Recent data indicate that resistance among HIV-1 isolates also emerges during dideoxyinosine (ddI) therapy. St. Clair et al., *Science*, 253, 1557 (1991). These characteristics confirm the resilience of HIV-1 and the need for more powerful strategies against this virus.

Drug targeting is a potentially attractive new approach to killing malignant or HIV-infected cells, an approach which can leave normal or uninfected tissue or cells unharmed. A decisive breakthrough in drug targeting was the advent of hybridoma technology, making many monoclonal antibodies (MoAbs) available in essentially limitless supply. To construct therapeutic reagents with selectivity for certain populations of cells, MoAbs or other cell targeting proteins are linked to bioactive moieties to form biotherapeutic agents referred to as immunoconjugates, immunotoxins or fusion proteins, which can combine the selectivity of the targeting moiety with the potency of the bioactive moiety. The choice of MoAb (or other targeting moiety) is based on the surface antigen profile of a target cell.

For the past decade, these types of biotherapeutic agents have been under investigation for the treatment of various cancers. Although these biotherapeutic agents have shown some potential to provide safe and effective therapy for human disease, many difficulties remain. Ideally, consistently locatable and reliable markers on target cells would permit the binding portion of biotherapeutic agents to completely avoid non-target tissue. In reality, cross-reactivity with antigens expressed by vital life-maintaining organs often gives rise to unacceptable complications in in vivo applications. There is also the potential that patients will demonstrate immune responses to the separate components of the biotherapeutic agents even though they may already be immunosuppressed by the course of their disease. Moreover, the cytotoxicity obtained in in vitro studies may be limited in clinical application due to a lack of potency in doses that can be tolerated by the patient Finally, solid tumors are difficult to penetrate thoroughly, and in hematologic malignancies, residual disease can cause relapse despite easier access to target cells in leukemias and lymphomas.

Toxicity studies using immunotoxins in mice and monkeys have not been predictive of the toxicity of the immunotoxins in clinical trials. For example, while no neurotoxicity was observed in monkeys treated with ricin A chain immunotoxins directed to B-cell surface antigens CD19 or CD22, when these immunotoxins were used in patients with lymphoma, a significant fraction showed peripheral neuropathy as well as aphasia (loss of speech). Similarly, no neurotoxicity was observed in preclinical animal studies using a recombinant ricin A chain immunotoxin of 454A12 mouse antitransferrin receptor monoclonal antibody or a natural pseudomonas exotoxin immunotoxin of OVB3 mouse anti-adrenocarcinoma monoclonal antibody. However, both immunotoxins caused lethal neurotoxicity with severe encephalopathy and brainstem inflammation when used in patients with cancer. Grossbard et al., *Blood*, 80, 863 (1992); Hertler et al., *J. Clin. Oncol.*, 7, 1932 (1989).

PAP has been used as the ribosomal-inhibitory (cytotoxic) moiety of an anti-CD19 immunotoxin in Phase I/II clinical trials of adult and pediatric patients with acute lymphoblastic leukemia under an Investigational New Drug Application (BB-IND-3864) approved by the Food and Drug Administration. Uckun F. M., *Brit. J. Haematol.*, 85, 435 (1993). Anti-CD19 PAP has been developed as an anti-leukemia agent since 1984 and generated very promising results in preclinical leukemia models, which provided the basis for ongoing clinical investigations. Uckun et al., *Leukemia*, 7, 341 (1993); Uchcm et al., *Journal of Exp. Med.*, 163, 347 (1986).

In a recently completed Phase I/II study, 18 patients with leukemia received escalating doses of anti-CD19 PAP at dose levels ranging from 0.1 µg/kg/day to 250 µg/kg/day×5 days and 10 patients received anti-CD19-PAP at a fixed dose level of 100 µg/kg/day×5 days. Uckun F. M., *Brit. J. Haematol.*, 85, 435 (1993). A maximum tolerated dose was not reached at the highest dose level of 250 µg/kg/day×5 days. Patients were given 1 hour i.v. infusions of anti-CD19-PAP on each of five days during one to three courses of treatment. Toxicities included capillary leak syndrome and myalgias. Importantly, no significant hepatic, renal, cardiac, or neurologic toxicity has been observed, and patients have not developed an immune response to either the PAP or monoclonal antibody moiety of anti-CD19 PAP. Thus, the clinical toxicity profile of PAP administered as an immunoconjugate is very different from the reported toxicity profiles of other RIPs. Of the 24 evaluable patients, 5 achieved a complete remission, 2 achieved a partial remission, 5 had partial responses but did not achieve remission, 9 had stable disease and only 3 progressed while on therapy. Four patients received treatment for minimal leukemia burden: therefore they are not evaluable for objective response. Thus, anti-CD19 PAP was able to penetrate bone marrow, liver, spleen, and lymph nodes leading to selective eradication of CD19-positive leukemia cells.

It has been reported that HIV-1 replication in normal CD4+ T cells can be inhibited in vitro by PAP. Zarling et al., *Nature*, 347, 92 (1990). Notably, targeting PAP to CD4+ T cells in vitro by conjugating it with MoAbs reactive with CD4+ T cells increased its potency >1,000-fold in inhibition of HIV-1 replication. Zarling et al., supra. Subsequent studies using clinical isolates of AZT-sensitive and AZT-resistant HIV-1 demonstrated that G17.2(anti-CD4)-PAP immunoconjugate exhibits potent anti-HIV activity against all isolates at nanomolar concentrations (Erice et al., *Antimicrobial Agents and Chemo.*, 37: 835 (1993)). However, the stability and efficacy of the G17.2(anti-CD4)PAP immunoconjugate in vivo is unclear.

Therefore, a need exists for an anti-T cell PAP immunotoxin with improved stability that is efficacious in vivo. Moreover, there is a continuing need for immunotoxins and methods of their use to target and inhibit or eliminate cell populations associated with various T cell-specific pathologies.

SUMMARY OF THE INVENTION

The present invention provides a biotherapeutic agent, e.g., an immunoconjugate or immunotoxin, comprising a monoclonal antibody specific to mammalian, e.g., human, T-cell/myeloid antigen CD7, linked to an effective amount of moiety, e.g., a polypeptide or a toxin, which has biological activity. These agents are active both in vitro and in vivo, and are useful to treat CD7+ T cell-specific diseases, such as certain cancers and certain viral infections, e.g., HIV infections associated with AIDS or ARC. As used herein, the term monoclonal antibody (MoAb) includes a fragment, a subunit or a derivative thereof, which is preferably covalently bonded or cross-linked to a biologically active moiety. Preferably, the moiety is pokeweed antiviral protein (PAP). The term "pokeweed antiviral protein" includes any moiety, e.g., a pokeweed protein, subunit, variant or derivative thereof such as PAP-II, PAP-S, and recombinant PAP, that has at least about 1%, preferably about 10%, and more preferably about 50%, the activity of native, purified pokeweed antiviral protein. The activity of a preparation of pokeweed antiviral protein can be determined by methods well known to the art, including methods described hereinbelow.

Thus, to treat cancer, the immunotoxin of the invention preferably comprises a cytotoxic amount of pokeweed antiviral protein. To inhibit or treat viral infections, the immunoconjugate of the invention preferably comprises an amount of pokeweed antiviral protein that is effective to inhibit viral infection and/or replication.

It is preferred that the immunoconjugate or immunotoxin of the present invention employs the monoclonal antibody TXU-7 or a biologically active subunit, fragment or derivative thereof, which binds to the CD7 antigen present at the surface of mammalian T-cell/myeloid cells, for example, the CD7 antigen present on the surface of leukemic blasts from T-cell ALL, AML and T-lineage lymphoma patients. A "biologically active" subunit or fragment of a monoclonal antibody has at least about 1%, preferably at least about 10%, and more preferably at least about 50%, of the binding activity of the monoclonal antibody. More preferably, the antibody utilized in the practice of the present invention has the binding specificity of the monoclonal antibody produced by hybrid cell line ATCC HB-12260.

Unlike immunoconjugates that rely on the expression of HIV-1 envelope proteins on infected cells to provide them with binding targets, the immunoconjugate of the present invention targets pokeweed antiviral protein to uninfected or latently infected $CD7^+$ cells using monoclonal antibodies against normal antigens on $CD7^+$ cells. It had been previously discovered by Applicant, and described in U.S. patent application Ser. No. 07/979,470, which application is incorporated herein by reference, that the internalization of protein antiviral protein-monoclonal antibody conjugates by monoclonal antibody receptor-mediated endocytosis results in increased delivery of pokeweed antiviral protein through the plasma membrane, as compared to the non-specific uptake that occurs at high pokeweed antiviral protein concentrations.

However, the pokeweed antiviral protein immunoconjugates disclosed in the '470 application display very poor in vivo stability and showed no anti-HIV activity in SCID mouse models of human AIDS. In contrast, as described hereinbelow, the immunoconjugate of the present invention showed potent anti-HIV-1 activity in a SCID mouse model of human AIDS without causing systemic toxicity. Moreover, in cynomolgus monkeys, the immunoconjugate of the present invention showed favorable pharmacokinetics with an elimination half-life of 8.1–8.7 hours. The monkeys treated with TXU-PAP at dose levels of 50 $\mu$g/kg/day×5 days or 100 $\mu$g/kg/day×5 days tolerated the therapy very well, without any significant clinical compromise or side effects, and at necropsy no gross or microscopic lesions were found. Thus, the immunoconjugate of the present invention exhibits surprising in vivo stability as measured by longer serum half-life and greater systemic exposure.

Hence, the present invention also provides a method to treat viral infection or inhibit viral replication in mammalian cells. The method comprises treating mammalian cells in vitro or a mammal having, or at risk of, a viral infection with an effective amount of the immunoconjugate of the present invention. One embodiment of the invention is a method to inhibit HIV replication or reduce viral burden in mammalian cells of the myeloid lineage and T-cells; thereby providing a method to treat patients with AIDS, ARC or asymptomatic patients infected with HIV-1 who have not yet developed AIDS. The immunoconjugate of the present invention may also be utilized in combination with at least one of the more conventional anti-AIDS agents, such as an anti-viral nucleoside analog, e.g., the reverse transcriptase inhibitor zidovudine (ZDV), without causing undesired side effects. The present method is especially suited for the treatment of patients infected with HIV stains that have become ZDV resistant.

Moreover, the present immunoconjugate may also provide the basis for an effective method to inhibit other lentiviruses (HTLV-1, etc.) and viruses other than lentiviruses that infect $CD7^+$ cells, viruses including, but not limited to, members of the herpes virus group (HSV, CMV, EBV), influenza viruses, rhinoviruses, papovaviruses (e.g., human papilloma), adenoviruses, hepatitis virus, and the like.

The invention further provides an immunotoxin useful to treat diseases or pathologies associated with undesirable T-cell proliferation, either alone or in combination with conventional therapies for such afflictions. Such pathologies include cancers, such as T-cell leukemias or lymphomas, acute myeloid leukemia, organ rejection, rejection of bone marrow transplants or autoimmune diseases such as systemic lupus erythematosus, rheumatoid arthritis, nonglomerular nephrosis, psoriasis, chronic active hepatitis, ulcerative colitis, Crohn's disease, Behret's disease, chronic glomerulonephritis (membranous), chronic thrombocytopenic purpura, and autoimmune hemolytic anemia The immunotoxin comprises a monoclonal antibody specific for the human T-cell myeloid antigen CD7, or a biologically active fragment or subunit thereof, linked to a cytotoxic amount of pokeweed antiviral protein. Preferably, the immunotoxin of the present invention employs the monoclonal antibody TXU-7 or a biologically active fragment or subunit thereof, which binds to the CD7 antigen present at the surface of mammalian cells.

Yet another embodiment of the present invention is a therapeutic method for the treatment of cancer. The method comprises parenteally administering to a mammal who is so afflicted with an amount of a pharmaceutical composition comprising an immunotoxin comprising monoclonal antibody TXU-7, or a biologically active fragment or subunit thereof, covalently linked to pokeweed antiviral protein, in combination with a pharmaceutically acceptable carrier. The amount of the composition administered is effective to inhibit or treat the cancer, e.g., it is a cytotoxic or an anti-neoplastic amount Preferably, the cancer to be treated is T-cell leukemia, lymphoma or acute myeloid leukemia (AML). The term "cytotoxic amount" is defined to mean an amount of pokeweed antiviral protein that is toxic to the target cell once the immunotoxin has associated with the cell.

Peripheral cancer cells that lack the target antigen may present complications in the treatment of certain patients. In these cases, combined or adjunctive therapies that exploit the diverse cytotoxic mechanisms offered by conventional chemotherapy or radiation can assist in the elimination of any cancer cells that lack the target antigen as well as in the suppression of immunotoxin-resistant mutants. Thus, one embodiment of the present invention comprises the administration of TXU-7-pokeweed antiviral protein in conjunction with, e.g., before, during or after, or a combination thereof, the administration of an effective amount of one or more conventional antineoplastic agents. Preferably, the antineoplastic agent employed is an anti-metabolite or a class I or a class III immunosuppressive agent. Preferably, the antineoplastic agent employed is cytarabine, methotrexate, trimetrexate, 5-fluorouracil, mercaptopurine, thioguanine, 5-azacytidine, floxuridine or 2"-chlorodeoxyadenosine, cyclophosphamide or etoposide. More preferably, the antineoplastic agent employed is cyclophosphamnide or etoposide. It is also preferred that the antineoplastic agent be combined with a pharmaceutically acceptable liquid carrier at a concentration of from about 10 mg/ml to about 30 mg/ml. In this embodiment of the invention, it is preferred that the antineoplastic agent, e.g., cyclophosphamide or cytarabine, be administered intravenously. Preferably, cyclophosphamide is administered at the rate of 0.5–3.5 L/M$^2$/24 hours.

DETAILED DESCRIPTION OF THE INVENTION

Figure 1A:
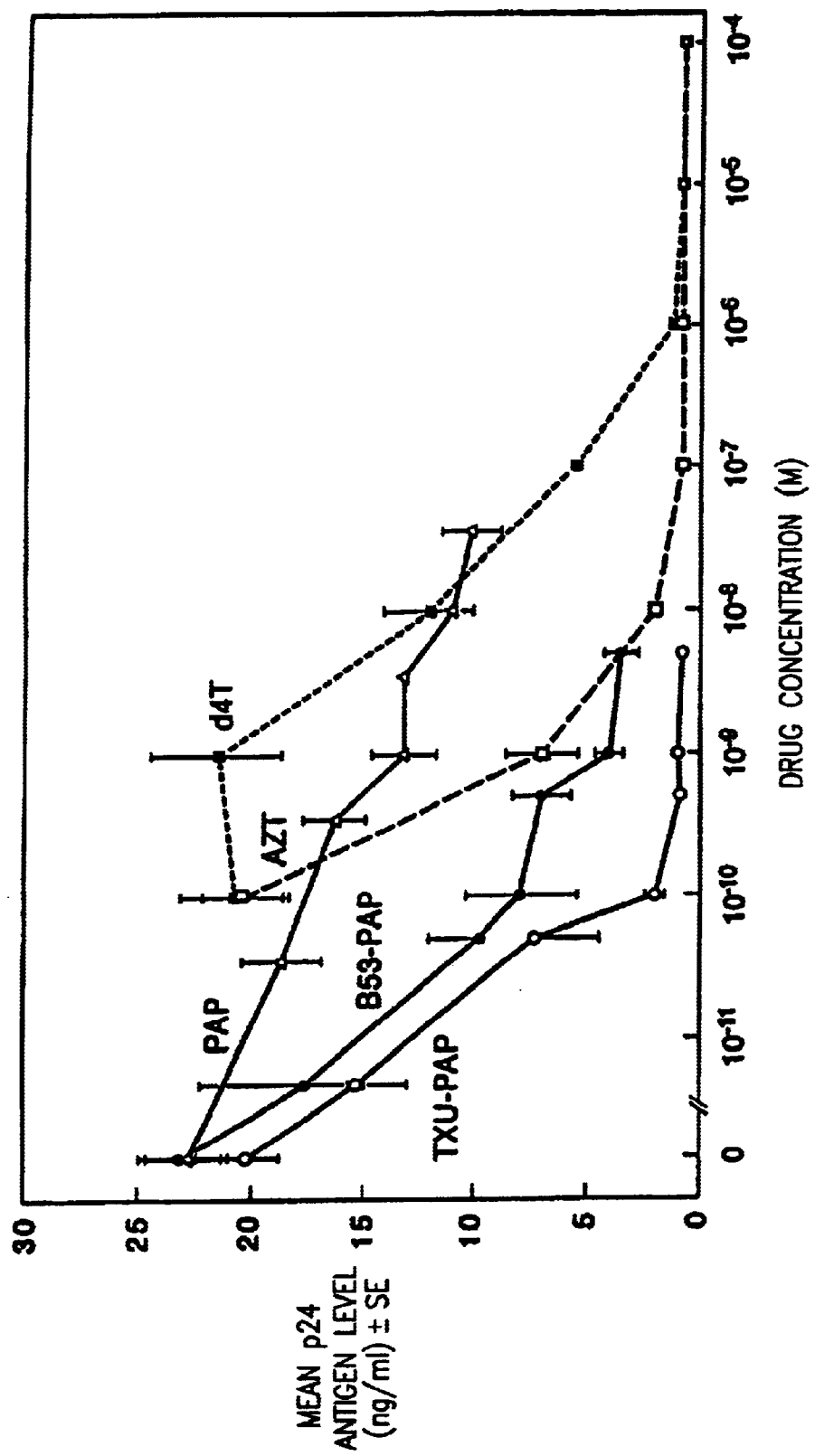
FIG. 1. In vitro anti-HIV-1 activity of TXU(anti-CD7)-pokeweed antiviral protein (PAP). The antiviral activity of TXU-PAP (o) against the HIV-1 strain HTLV$_{mB}$ was evaluated in side by side comparison with B53(anti-CD4)-PAP (o), unconjugated PAP (Δ), AZT (□), and d4T (■) using in vitro p24 EIA (panel A) and RT assays (panel B). The background cpm in uninfected control cultures from the RT assays (i.e., 116±9 cpm) is also shown (o).

The present invention is directed to an immunotoxin or immunoconjugate useful in the treatment of mammalian cancer and viral infections, including infections by retroviruses and lentiviruses such as HTLV-I, HTLV-II, SIV, HIV-1 and HIV-2 and the like. Specifically, the present invention provides an immunoconjugate useful in the treatment of ARC, AIDS, or asymptomatic HIV or HTLV infection. The invention also is directed to an immunotoxin useful in the treatment of cancer, including ALL and AML.

I. Immunotoxins

Several requirements must be fulfilled for an immunotoxin to be effective. First of all, the immunotoxin should be specific and should not react with tissues that do not express the target antigen to the extent that it is detrimental to the target mammal. Pastan et al., Cell, 47, 641 (1986). Binding to tissues that do not express antigen can be reduced by removal of the nonspecific natural cell-binding subunits or domains of the biotherapeutic moiety, e.g., a plant glycoprotein toxin or antiviral agent. Furthermore, because plant glycoprotein toxins contain mannose oligosaccharides that bind to cells of the reticuloendothelial system and, in some cases, also contain fucose residues that are recognized by the receptors on hepatocytes, deglycosylation of plant toxins may be required to, avoid rapid clearance and potential cytotoxic effects on these cells. Secondly, the linkage of the toxin to the antibody should not substantially impair the capacity of the antibody to bind to the antigen. Third, the immunotoxin must be effectively internalized into the endosomic vesicles. Thus, toxins directed by monoclonal antibodies to surface receptors that are normally internalized may be more active than those directed toward noninternalizing cell surface molecules. Fourth, the active component of the toxin must translocate into the cytoplasm. Finally, for in vivo therapy, the linkage between the MoAb and the toxin must be sufficiently stable to remain intact while the immunotoxin passes through the tissues of the mammal to its cellular site of action.

The first generation of heterobifunctional cross-linkers used to bind the toxin to the monoclonal antibody generated disulfide bonds that were unstable in vivo. This problem was solved in part by the synthesis of more stable cross-linkers, which used phenyl or methyl groups, or both, adjacent to the disulfide bond, to restrict access to the bond. These various approaches can be in conflict; for example, the removal of the B chain of ricin reduces nonspecific binding but also reduces the capacity of the residual A-chain monoclonal antibody conjugate to translocate across the endosomic vesicle membrane.

The activity of an immunotoxin is initially assessed by measuring its ability to kill cells with target antigens on their surfaces. Because toxins act within the cells, receptors and other surface proteins that naturally enter cells by endocytosis usually are appropriate targets for immunotoxins, while surface proteins that are fixed on the cell surface do not.

However, if several antibodies recognizing different epitopes on the same cell surface protein are available, it is useful to test them all. This is because some antibodies, perhaps by producing a conformational change in the target protein, may more efficiently induce internalization or direct intracellular routing to an appropriate location for toxin translocation. May et al., *Cell Immunol.*, 135, 490 (1991). Also, if the receptors are efficiently internalized, it is possible to employ an immunotoxin that does not bind as strongly to the receptor, due to the chemical modification(s) needed to prepare the immunotoxin. Wingham et al., *Proc. Natl. Acad. Sci. USA*, 84, 2474 (1987).

A. Monoclonal Antibodies

Monoclonal antibodies (MoAbs) are produced by the fusion of spleen lymphocytes with malignant cells (myelomas) of bone marrow primary tumors. Milstein, *Sci. Am.*, 243, 66 (1980). The procedure yields a hybrid cell line, or hybridoma, arising from a single fused cell hybrid, or clone, which possesses characteristics of both the lymphocytes and myeloma cell lines. Like the lymphocytes (taken from animals primed with sheep red blood cells as antigens), the fused hybrids or hybridomas secrete antibodies (immunoglobulins) reactive with the antigen. Moreover, like the myeloma cell lines, the hybrid cell lines are immortal. Specifically, whereas antiser derived from vaccinated animals are variable mixtures of antibodies which cannot be identically reproduced, the single-type of immunoglobulin secreted by a hybridoma is specific to one and only one determinant on the antigen, a complex molecule having a multiplicity of antigenic molecular substructures, or determinants (epitopes). Hence, monoclonal antibodies raised against a single antigen may be distinct from each other depending on the determinant that induced their formation. However, all of the antibodies produced by a given clone are identical. Furthermore, hybridoma cell lines can be reproduced indefinitely, are easily propagated in vitro and in vivo, and can yield monoclonal antibodies in extremely high concentrations.

Monoclonal antibodies have largely been applied clinically to the diagnosis and therapy of cancer, the modulation of the immune response to produce immunosuppression for treatment of autoimmune and graft versus host diseases (GVHD) and for prevention of allograft rejection. Human monoclonal antibodies have also been applied clinically against cytomegalovirus, *Varicella zoster* virus, and the various specific serotypes of *Pseudomonas aeruginosa, Escherichia coli*, and *Klebsiella pneumoniae*.

Monoclonal antibodies useful in the present invention are produced using well known hybridoma fusion techniques (G. Kohler and C. Milstein, *Eur. J. Immunol.*, 6, 511 (1976); M. Shulnan et al., *Nature*, 276, 269 (1978)). As indicated above, the present invention uses a monoclonal antibody directed against T-cells. Preferably, the specific antibody is specific for $CD7^+$ T cells. More preferably, the antibody is TXU-7.

1. TXU-7

The MoAb TXU-7 (murine IgG1:kappa subclass) recognizes the CD7/41 kDa antigen expressed on human T-lineage lymphoid cells and, most importantly, on leukemic progenitor (stem) cells in T-lineage lymphoid malignancies.

B. Toxins

The limited efficacy of many unmodified MoAbs has led to an alternative approach, that is, the use of these agents as carriers for toxins. An array of toxins of bacterial and plant origin have been coupled to MoAbs for production of immunotoxins. The strategy is to select from nature a cytotoxic protein and then to modify the cytotoxic protein so that it will no longer indiscriminately bind and kill normal cells, but will instead kill only the cells expressing the antigen bound by the MoAb. To be optimally effective, such an approach requires that internalization of relatively small numbers of cytotoxic molecules be lethal to target cells, as there are limited receptor sites on the cell surface for a given MoAb. The toxins produced by certain bacteria and plants that inactivate cellular protein synthesis meet this criteria as, unlike most chemotherapeutic agents which act in a stoichiometric manner, they are catalytic in their lethal activity. In general, less than ten toxin molecules in the cytoplasm of a cell are sufficient to kill the cell.

Two classes of toxins that inactivate protein synthesis have been widely employed in the construction of immunotoxins. The first class consists of intact toxins, such as intact ricin. See, e.g., Leonard et al., supra. These toxins cannot be safely applied in vivo because of lethal toxicity. The second group of toxins are referred to as hemitoxins. Lethally inhibiting protein synthesis in a complementary manner, hemitoxins covalently modify the ribosome such that it can no longer productively interact with elongation factor 2. This latter family of toxins includes pokeweed antiviral protein (PAP), ricin, abrin, gelonin, saporin, and alpha-sarcin. The ribosome inactivating proteins derived from plants consist of either two chains, including a binding chain and catalytic chain (e.g., ricin), or a single catalytic chain alone (e.g., PAP or saporin).

1. PAP

PAP is a member of the hemitoxin group of toxins and thus inactivates ribosomes by the specific removal of a single adenine from the conserved loop sequence found near the 3' terminus of all larger rRNAs. Irin et al., *Pharmacology and Therapeutics*, 55, 279 (1992). This specific depurination greatly reduces the capability of elongation factors to interact with ribosomes and results in an irreversible shut-down of protein synthesis. Irvin et al., cited supra. Furthermore, PAP is one of the most active ribosomal inactivating proteins. In a comparison of cytotoxicity of anti-mouse IgG immunotoxins gelonin, ricin A chain, momordin, dianthin 32, saporin, and PAP, the PAP constructs were among the most potent immunotoxins tested. Irvin et al., cited supra. Bolognesi et al., *Clin. Exp. Immunol.*, 89, 341 (1992).

There are three subtypes of pokeweed antiviral protein (PAP) the expression of which are dependent upon the season. PAP is found in spring leaves of pokeweed (*Phytolacca americans*), PAP-II is found in late summer leaves, and PAP-S is found in seeds. Irvin, *Pharmacol. Ther.*, 21, 371 (1983). Small differences exist in their sizes (all are approximately 29,000 MW) and there are only small differences, if any, between their ability to inhibit ribosomes catalytically. Houston et al., in "*Immunological Antibody Conjugates in Radioimaging and Therapy of Cancer,*" C. W. Vogel, ed., New York, Oxford University Press, p. 71 (1987).

C. Production and Purification of TXU-7-PAP

Preferred TXU-7-PAP immunotoxins for use in the present method are formed by linking an effective cytotoxic or antiviral amount of PAP molecules to each molecule of TXU-7. For example, a reagent useful in the practice of the invention includes one to two PAP molecules per TXU-7 molecule. Preferably, a composition of the invention includes about a 1:1 mixture of a) one molecule of PAP/molecule of TXU-7, and b) two molecules of PAP/molecule of TXU-7. Preferably, a composition of the invention contains mainly 1 or 2 PAP molecules per intact TXU-7 monoclonal antibody molecule, free TXU-7 MoAb, and free PAP. More preferably, in 1 mg of the composition, there are 420 μg of 180 kDa TXU-7-PAP containing one molecule of PAP attached to each molecule of TXU-7 MoAb, 395 μg of 210 kDa TXU-7-PAP containing two molecules of PAP attached to each molecule of TXU-7 MoAb, 130 μg of unconjugated free TXU-7 MoAb, and 55 μg, of unconjugated free PAP.

The particular TXU-7-PAP employed in Examples 4 and 5 hereinbelow is prepared by linking TXU-7 MoAb to PAP as described in U.S. Pat. No. 4,831,117, which is incorporated herein by reference. A further description of the production and purification of TXU-7-PAP can be found in Examples 1–3. However, TXU-7 can be linked to effective amounts of PAP by other means disclosed in the art, including those taught in U.S. Pat. Nos. 4,363,758 (Masuho et al.); U.S. Pat. No. 5,167,956 (Neville, Jr. et al.) and U.S. Pat. No. 4,340,535 (Voisin et al). For example, in addition to N-succinimidyl 3-(2-pyridyldithio)propionate (SPDP), 4-succinimidyloxycarbonyl-methyl-(2-pyridyldithio)-toluene (SMPT) and N-succimidyl 6-[3-(2-pyridyldithio) propionamido]hexanoate (LC-SPDP) may be used as linking agents.

D. Modes of Administration of TXU-7-PAP

The immunotoxin of the invention, or a combination thereof, can be formulated as a pharmaceutical composition and administered to a human or other mammal afflicted with cancer or infected with a virus, preferably as a unit dosage form comprising an effective amount of one or more of the immunotoxins in combination with a pharmaceutically acceptable carrier or vehicle, and/or in combination with other therapeutic agents.

1. Dosage Forms

It is preferred that the TXU-7-PAP immunotoxin of the present invention be parenterally administered, i.e., intravenously, or subcutaneously by infusion or injection. Solutions or suspensions of the immunotoxin can be prepared in water, or a physiological salt solution such as isotonic saline or PBS, optionally mixed with a nontoxic surfactant. More preferably, the immunotoxin is prepared at a concentration of about 1.0 mg/mL in 40 mM sodium phosphate buffer, pH 7.5, containing 150 mM sodium chloride and is further diluted in 0.9% saline for intravenous administration.

Although it is preferred that the immunotoxin be administered as a liquid composition as described herein, it can be administered with a variety of other carriers. For example, dispersions can also be prepared in glycerol, liquid polyethylene glycols, DMA, vegetable oils, triacetin, and mixtures thereof. Under ordinary conditions of storage and use, these preparations may contain a preservative to prevent the growth of microorganisms. Additionally, more specific delivery of the immunotoxin to the lungs may be accomplished via aerosol delivery systems. The compositions suitable for aerosol delivery can include adipot formulations such as a liposome of suitable size.

The compositions suitable for injection or infusion can include sterile aqueous solutions or dispersions or sterile powders comprising the immunotoxin which are adapted for the extemporaneous preparation of sterile injectable or infusible solutions or dispersions. In all cases, the ultimate composition must be sterile, fluid and stable under the conditions of manufacture and storage. The liquid carrier or vehicle can be a solvent or liquid dispersion medium comprising, for example, water, ethanol, a polyol (for example, glycerol, propylene glycol, and liquid polyethylene glycols, and the like), vegetable oils, nontoxic glycerol esters, lipids (for example, dimyristoyl phosphatidyl choline) and suitable mixtures thereof. The proper fluidity can be maintained, for example, by the formation of liposomes, by the maintenance of the required particle size in the case of dispersion or by the use of nontoxic surfactants. The prevention of the action of microorganisms can be accomplished by various antibacterial and antifungal agents, for example, parabens, chlorobutanol, phenol, sorbic acid, thimerosal, and the like. In many cases, it will be desirable to include isotonic agents, for example, sugars, buffers or sodium chloride. Prolonged absorption of the injectable compositions can be brought about by the inclusion in the compositions of agents delaying absorption, for example, aluminum monostearate hydrogels and gelatin.

Sterile injectable or infusable solutions are prepared by incorporating the immunotoxin in the required amount in the appropriate solvent with various of the other ingredients enumerated above, and as required, followed by filter sterilization. In the case of sterile powders for the preparation of sterile injectable or infusable solutions, the preferred methods of preparation are vacuum drying and the freeze drying techniques, which yield a powder of the active ingredient plus any additional desired ingredient present in the previously sterile-filtered solutions.

Furthermore, suitable formulations for the immunotoxin of the present invention include those suitable for oral, rectal, nasal, topical (including, ocular, and sublingual) or vaginal administration or in a form suitable for administration by inhalation or insufflation. The formulations may be prepared by any of the methods well known in the art of pharmacy. Such methods include the step of bringing into association the immunotoxin with liquid carriers or finely divided solid carriers or both and then, if necessary, shaping the product into the desired formulation.

Pharmaceutical formulations suitable for oral administration may conveniently be presented as discrete units such as capsules, sachets, or tablets, each containing a predetermined amount of the active ingredient; as a powder or granules; as a solution, a suspension or as an emulsion. The active ingredient may also be presented as a bolus, electuary or paste. Tablets and capsules for oral administration may contain conventional excipients such as binding agents, fillers, lubricants, disintegrants, or wetting agents. The tablets may be coated according to methods well known in the art. Oral liquid preparations may be in the form of, for example, aqueous or oily suspensions, solutions, emulsions, syrups or elixirs, or may be presented as a dry product for constitution with water or other suitable vehicle before use. Such liquid preparations may contain conventional additives such as suspending agents, emulsifying agents, non-aqueous vehicles (which may include edible oils), or preservatives.

The immunotoxin of the present invention may also be formulated for intra-nasal or ocular adminion. In this form of administration, the active ingredient may be used as a liquid spray or dispersible powder or in the form of drops. Drops, for example, eyedrops, may be formulated with an aqueous or non-aqueous base also comprising one or more dispersing agents, solubilizing agents or suspending agents. Liquid sprays are conveniently delivered from pressurized packs.

For administration by inhalation, the immunotoxin is conveniently delivered from an insufflator, nebulizer or a pressurized pack or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount.

Alternatively, for administration by inhalation of insufflation, the immunotoxin may take the form of a dry powder composition, for example, a powder mix of the compound or a suitable powder base such as lactose or starch. The powder composition may be presented in unit dosage form in, for example, capsules or cartridge or e.g., gelatin or blister packs from which the powder may be administered with the aid of an inhaler of insufflator.

Additionally, the immunotoxin of the present invention is well suited to formulation in controlled release dosage forms. The formulations can be so constituted that they release the active dry ingredient only or preferably in a particular physiological location, optionally over a period of time. The coatings, envelopes, and protective matrices may be made, for example, from polymeric substances or waxes. The compounds can also be delivered via patches for transdermal delivery, subcutaneous implants, infusion pumps or via release from implanted depot sustained release dosage forms.

2. Dosages

The dosage of the immunotoxins in the compositions of the invention can be varied widely, in accord with the size, age and condition of the mammal and the disease. For example, the dose of TXU-7 PAP to inhibit cancer is about 10 to about 100,000 ng/ml, preferably about 100 to about 10,000 ng/ml. Thus, for an adult, the dose of TXU-7 PAP administered to inhibit cancer is about 1 μg/kg to about 1000 μg/kg, preferably about 50 μg/kg to about 500 μg/kg, and more preferably about 10 μg/kg to about 250 μg/kg. The dose of TXU-7 PAP administered to inhibit viral infection is about 1 μg/kg to about 750 μg/kg, preferably about 5 μg/kg to about 250 μg/kg, and more preferably 10 μg/kg to about 50 μg/kg. Dosages are administered with a frequency based on the plasma half life of TXU-7-PAP immunotoxins in a given patient, as determined by solid phase ELISA. Higher doses can be employed in some cases, and the doses can readily be adjusted to provide appropriate amounts of the immunotoxin to children using the above formula The invention will be further described by reference to the following detailed examples.

EXAMPLE 1

Pokeweed Antiviral Protein (PAP)

A. Preparation and Purification of Pokeweed Antiviral Protein (PAP)

Pokeweed (*Phytolacca americans*) leaves are harvested in the month of May from the wild in Caldwell County, Tex. PAP (Lot #P-1993) from these spring leaves, used in the production of clinical TXU-7-PAP immunotoxin described hereinbelow, was prepared according to the following procedure: Five kg of fresh or frozen pokeweed leaves were juiced in a kitchen juicer (Acme model 5001) and clarified by centrifugation. The PAP containing supernatant was adjusted to 40% saturation by the addition of solid ammonium sulfate and centrifuged at 10,000 ×g for 45 minutes at 40° C. The resulting supernatant was adjusted to 90% saturation with solid ammonium sulfate and the precipitate collected by centrifugation.

The pellet (containing precipitated PAP) was dissolved in a minimum volume of 10 mM Tris-HCl, pH 8.0, and dialyzed against the same solution overnight. The dialysis solution was changed and dialysis continued for 6–12 hours. The dialyzed ammonium sulfate fraction was then passed through a 2 cm bed of coarse, acid-base washed DEAE cellulose (DE52 and CDR, Whatman), packed in a Buchner funnel, and the filtrate applied to a 5×48 cm S-Sepharose column equilibrated with 20 mM potassium phosphate buffer at pH 6. The column was washed with 1 L of equilibration buffer and the protein eluted with a 2500 mL linear gradient from 0–0.5 KCl in equilibration buffer.

The PAP peak, eluting between approximately 700 mL and 1000 mL, was concentrated by ultrafiltration over a PN-30 membrane (Amicon) and frozen at −70° C. This procedure allowed the processing of 5 kg of pokeweed leaves per day, routinely yielded 80–85 mg of purified PAP per kg of Pokeweed leaves, and 400–1000 mg of purified PAP within one week.

B. Quality Control of Pokeweed Antiviral Protein (PAP)

1. SDS-PAGE

To biochemically confirm the purity of PAP toxin, 1.5–3 μg samples of purified PAP were analyzed by SDS-PAGE using 15% separating gels and the Bio-Rad Mini Protean II slab gel, under denaturing conditions according to the method described by Laemmli in *Nature*, 227, 680 (1970). Gels were stained with Coomassie Blue or the silver stain kit obtained from Bio-Rad Laboratories, destained, dried, and scanned using a Beckman DU62 Spectrophotometer and Gel Scan Soft-Pac Module software (Beckman Instruments, Fullerton, Calif.) as described hereinbelow. The purity of PAP was further confirmed by Western blot analysis using a rabbit anti-PAP primary antibody and a goat-anti-rabbit IgG secondary antibody conjugated to alkaline phosphatase.

SDS-PAGE of PAP revealed a single 29 kDa protein band. A densitometer scan of the Coomassie Blue stained gel showed that PAP represented 99.0% of the protein in the lane. In addition, a single band was identified by the anti-PAP primary antibody during the immunoblotting procedure.

2. High Performance Liquid Chromatography (HPLC)

The purity of PAP was also assessed by ion exchange HPLC using an SP-5PW 7.5×75 mm analytical column and Beckman System Gold HPLC System and System Gold Chromatography Software (Beckman Instruments, San Ramon, Calif.). A flow rate of 1 ml/minute was used and PAP eluted with a 20 minute, 0–300 mM potassium chloride gradient in 20 mM potassium phosphate buffer, pH 7.

Purified PAP characteristically eluted as a sharp peak with a retention time of 12–13 minutes when subjected to a 20 minute, 0–300 mM potassium chloride (KCl) gradient in 20 mM potassium phosphate buffer, pH 7.0, on an SP-5PW 7.5×75 mm analytical cation exchange HPLC column. Automated integration analysis of the distinct HPLC peak indicates that PAP represents 99.0% of the total protein present in the preparation.

3. N-terminal Amino Acid Sequence of Purified PAP

Thirty mg of highly purified PAP protein in 100 μl of 10 mM sodium phosphate buffer, pH 7.0, was sequenced at the University of Minnesota Microchemical Facility according to the automatic degradation procedure originally described by Edman and Begg (1967) and modified by Hunkapiller et al (1983) using an Applied Biosystems Model 470A gas phase protein sequencer (Edman et al., *Eur. J. Biochemisty*, 1, 80 (1967); Hunkapiller et al., *Methods in Enzymol.*, 91, 399 (1983). High performance liquid chromatography using an on-line Model 120A HPLC (Applied Biosystems, Foster City, Calif.) was used to identify the phenylthiohydantoin amino acids. HPLC chromatograms of the sample, generated for each Edman degradation cycle, were compared to similar HPLC chromatograms obtained for phenylthiohydantoin amino acid standards.

Amino acid residues were assigned following 43 cycles of the Edman degradation reaction. The amino terminal sequence agrees with a sequence of 32 amino acid residues which has been previously published by Houston et al., *J. Biol. Chem.*, 258, 9601 (1983). This sequence differs from one of 30 residues reported by Ready et al. in that a lysine residue was found at position 15 (instead of phenylalanine)

and an arginine residue was found at position 24 (instead of glutamine). Ready et al., *J. Biol. Chem.*, 259, 15252 (1984). A cysteine residue has been tentatively assigned at position 34 pending further sequencing experiments performed on samples of PAP which have been derivatized in order to identify the resulting modified cysteine residue. Importantly, identical sequence data was obtained on 3 different preparations of PAP confirming the reproducibility of the purification procedure. Notably, sequence data was obtained on 1 nmole of this highly purified preparation of PAP.

4. Cell-Free Protein Synthesis Inhibition Assay of PAP Toxicity

The ribosome-inhibiting activity of PAP was analyzed in a cell-free translation system obtained in kit form from Promega Biotec, Inc. (Madison, Wis.) and based on a method developed by Pelham and Jackson. Pelham et al., *Eur. J. Biochem.*, 67, 247 (1976). This system consists of the following: nuclease-treated rabbit reticulocyte lysate (35 µL), 1 mM amino acid mixture minus leucine (1 µl), [$^3$H] leucine (183 Ci/mmol, 1 mCi/mL, Amersham Corp., Arlington Hts, Ill.), 5 µl of brome mosaic virus RNA (2 µL of 0.5 µg/µL stock), and water or buffer to bring the final volume to 50 µL per assay tube. Samples are diluted in PBS and 2.5–5 µL amounts were added to the lysate. Control samples minus toxin were set up in triplicate. At 0 hr (immediately after adding [$^3$H]-leucine and RNA and mixing gently to start the reaction), 10 µL aliquots were removed from the control and mixed with 1 mL 1 N NaOH to stop the reaction. The control toxin-treated samples were incubated an additional 60 minutes at 37° C., at which time 10 µL samples were again removed to NaOH, mixed, and 50 µL of 30% $H_2O_2$ added to decolorize the samples.

Following 10 minutes incubation at 37° C., the tubes were transferred to an ice bath and 2 mL of cold 4% casamino acids followed by 2 mL of cold 50% trichloroacetic acid (TCA) were added to precipitate the synthesized protein. After 30 minutes on ice, the samples were filtered through GF/F glass microfiber filters (Whatman, Hillsboro, Oreg.). The extent of protein synthesis inactivation is determined as percent control response=100 ×([$^3$H]-leucine incorporation [mean cpm at t60'–mean cpm at t0] for the toxin-treated samples)/([$^3$H]-leucine incorporation [mean cpm at t60'–mean cpm at t0] for the untreated control).

Purified PAP batches (n=6) used in preparing clinical batches of TXU-7-PAP immunotoxin had, fro example, an IC (mean SE) value of 0.34±0.06 ng/mL (range=0.17–0.58 ng/mL, 12.2 pM; range=6.0–20 pM) and an IC value of 3.7±1.1 ng/mL (range=0.63–7.5 ng/mL, 130.37 pM; range= 22–263 pM) when tested for their ribosome inhibitory activity in the rabbit reticulocyte cell-free translation assay.

Table 1, below, summarizes the quality control analysis data on purified PAP.

TABLE 1

QUALITY CONTROL ANALYSIS OF
PURIFIED POKEWEED ANTIVIRAL PROTEIN (PAP)

| Test Parameters | Results |
| --- | --- |
| Yield | 80 mg purified PAP/kg leaves |
| Purity | |
| SDS-PAGE | 99.9% |
| HPLC | 99.9% |
| Molecular Weight | 29 kDa |
| Amino Acid Composition | Confirmatory |
| Sterility Test | Negative |
| Acute Toxicity in Mice | $LD_{50}$ (i.v.) 150 mg/mouse |

EXAMPLE 2

Monoclonal Antibody TXU-7

A Preparation of Monoclonal Antibody TXU-7

TXU-7 MoAb was originally obtained from culture supernatants of the hybridoma cell line. Large scale production of TXU-7 MoAb was performed according to the general recommendations of the Center for Biologics Evaluation and Research (CBER), FDA (detailed in "Points to Consider in the Manufacture and Testing of Monoclonal Antibody Products for Human Use", 1994 document of the FDA), using a dedicated ACUSYST-JR. (69.8 cm wide×66 cm deep×52 cm high) benchtop automated hollow-fiber cell culture system (Cellex Biosciences, Inc., Coon Rapids, Minn.).

The flowpath containing one hollow fiber bioreactor (surface area=1.1 m$^2$) with 10,000 daltons molecular weight cut-off membranes was inoculated with 2.4×10$^8$ viable hybridoma cells, secreting TXU-7 MoAb, in a volume of 45 mL of FBS (10% v/v)-supplemented RPMI without antibiotics. After inoculation, the intracapillary space (ICS) was continually recirculated with serum-free and antibiotic-free RPMI. Fetal bovine serum (FBS) supplemented RPMI was used only in the extracapillary space (150 mL) of the bioreactor and unsupplemented RPMI was circulated through the ICS of the hollow fiber system to provide nutrients and dissolved oxygen, and to remove waste products. Cell metabolism was continually monitored on line via dissolved oxygen and pH probes which are calibrated every other day. Daily samples from the ECS were assayed for pH, bicarbonate, glucose, lactate, dissolved oxygen, and carbon dioxide ($pO_2$ and $pCO_2$), as well as mouse IgG levels. The rate at which medium was oxygenated in the gas exchange cartridge is controlled by the bellows pump in the ACUSYST-JR. The supernatant was harvested at a rate of 100–200 mL/day. Concomitantly and at the same rate, freshly prepared FBS-supplemented RPMI was delivered to the ECS (extracapillary space).

The concentration of TXU-7 MoAb in the ECS was determined by a solid phase ELISA as follows: The wells of Falcon Micro Test 111 culture plates (Cat. #3070) were coated with 50 µL of affinity purified goat anti-mouse IgG (100 µg/mL; Cappel, Organon Teknika Corp., Westchester, Pa.). After overnight incubation at 37° C., the plates were washed three times with PBS containing 0.05% Tween 20 (Sigma Chemical Co., St. Louis, Mo.). Background sites on the well surface were blocked with 100 µL/well PBS supplemented with 2.5% calf bovine serum (Hyclone, Logan, Utah) for 2 hours at 37° C. Subsequently wells were washed three times with PBS containing 0.05% Tween 20 prior to addition of the test samples. Test samples (50 µL/well in triplicate) were undiluted, 1:100 diluted, or 1:500 diluted supernatants from the ECS. For standards, purified TXU-7 MoAb was serially diluted in PBS containing 2.5% calf bovine serum to concentrations of 0.01–10.0 µg/mL and 50 µL samples from each dilution are added to triplicate wells. After a 2 hour incubation at 37° C., the plates were washed three times with PBS containing 0.05% Tween 20. Fifty µL of a 1:500 dilution of goat anti-mouse IgG conjugated to peroxidase (Cappel) were then added to each well. After a 30 minute incubation at 37° C., the plates were washed three times in PBS containing 0.05% Tween 20, and 50 μL of ABTS (peroxidase substrate system; Kirkegaard & Perry, Gaithersburg, Md.) was added to each of the wells. The plates were read 15 minutes later at 405 nm absorbance using the ELISA reader (Dynatech MR 580 Micro ELISA Autoreader). The antibody concentrations of the ECS supernatants were determined from a standard curve which is generated by regression analysis using known amounts of purified TXU-7 MoAb.

During the 72-day production run, the RPMI feed rate was increased in a step-wise fashion from 25 mL/hr (=600 mL/day) to 360 mL/hr (=8640 mL/day) in response to increased glucose consumption, to maintain the glucose concentration in the ECS at 340–440 mg%. $pO_2$ was maintained at 120–190 mm Hg and $pCO_2$ was maintained at 24–80 mm Hg. The pH was maintained in the range of 7.0–7.2 units by controlling the rate of $CO_2$/air mixture through the gas exchange cartridge and by controlling the lactic acid concentration in the ECS. Bicarbonate ranged from 15 to 25 mmol/L and lactate ranged from 2.5 to 9.5 mmol/L. The DXU-7 IgG1 concentration in the ECS of the ACUSYST-JR bioreactor increased from a level of 34 μg/mL on day 5 to a maximum of 336 μg/mL on day 46. A total of 1.2 grams of TXU-7 IgG was harvested from the ECS, in a total volume of 7.55 L, during the course of the production run. The average concentration of the TXU-7 MoAb in the ECS was 0.16 g/L (160 mg/L).

B. Purification of Monoclonal Antibody TXU-7

TXU-7 MoAb (Lot #A-1993) was purified from the harvested ACUSYST-JR culture supernatants using the Affi-Prep Protein A MoAb purification system from Bio-Rad Laboratories (Hercules, Calif.) set up in a 49 cu. ft. chromatography cabinet (Model 450 Puffer Hubbard, New York, N.Y.) equipped with two 15 watt germicidal ultraviolet (UV) lamps.

The support consists of a highly purified preparation of Protein A cross-linked to a hydrophilic polymeric bead. The resin is sanitizable with 1 N NaOH and stable at pH 2–14 and to pressures up to 1,000 psi. The Protein A preparation is pyrogen-free, non-toxic, and has a leakage of less than 5 ng/mL of eluate.

The harvested culture supernatant was first centrifuged to remove cell debris and then concentrated to 5 mg/mL, using Centriprep-30 concentrating devices (Amicon, Beverly, Mass.). The supernatant was then diluted 1:1 with binding buffer (1.5 M glycine+3 M NaCl, pH 8.9) and applied to the Affi-Prep Protein A column which was previously equilibrated with the same buffer. The column was washed with 15 bed volumes of binding buffer and the MoAb subsequently eluted at pH 4. The purified antibody was then neutralized, concentrated, and dialyzed against 40 mM sodium phosphate buffer, pH 7.5, containing 150 mM sodium chloride, and filter-sterilized. Antibody concentrations were determined spectrophotometrically using an $E_{280}^{1\%}$ nm value of 1.4. All buffers were made up in endotoxin-flee water (Baxter Healthcare Corp., Deerfield, Ill.) and filter-sterilized just before use. The Affi-Prep Protein A column was finally washed with 100 mM citric acid, pH 3.0, to remove any remaining proteins and to inactivate any virus particles trapped in the resin.

Using the Affi-Prep Protein A resin, up to 100 mg of TXU-7 MoAb was purified per day in a single step process from the harvested ACUSYST-JR supernatants. Aliquots from all batches of Protein A-purified JXU-7 MoAb were analyzed by polyacrylamide gel electrophoresis under denaturing conditions (SDS-PAGE). After staining and destaining, the 5% separating gels were dried and subsequently scanned using a Beckman DU-62 spectrophotometer and Gel Scan Soft-Pac Module software.

Samples of purified TXU-7 MoAb (1.5–2.5 μg) were analyzed by SDS-PAGE (Mini-Protean III slab gel apparatus of Bio-Rad Laboratories) according to the method of Laemmli, using a 5% separating gel (or 15% under reducing conditions) and 4% stacking gel. Laemmli, cited supra. Pre-stained molecular weight standards (Amersham Corp., Arlington Hts., Ill.) included lysozyme (14.3 kDa), trypsin inhibitor (21.5 kDa), carbonic anhydrase (30 kDa), ovalbumin (46 kDa), bovine serum albumin (69 kDa), phosphorylase B (97.4 kDa subunit), and myosin (200 kDa subunit). Gels were stained with Coomassie Blue G-250, destained in 10% acetic acid/30% methanol, dried, and subsequently scanned using a Beckman DU62 spectrophotometer and Gel Scan Soft-Pac Module software (Beckman Instruments, Fullerton, Calif.). When greater staining sensitivity was desired, a silver stain kit obtained from Bio-Rad Laboratories was utilized to visualize the protein bands after SDS-PAGE. Merril et al., *Science*, 211, 1437 (1981).

Briefly, gels were transferred to a 40% methanol, 10% acetic acid solution and stored at room temperature overnight. Gels were washed 2 times in 10% ethanol, 5% acetic acid followed by a 5 minute incubation in an oxidizer solution. Subsequently, 3 washes in distilled $H_2O$ were performed, followed by a 20 minute incubation in a silver nitrate solution. Gels were washed once in distilled $H_2O$ for 1.0 minute and placed in a developer solution (containing sodium carbonate and paraformaldehyde) for 30 seconds. The developer solution was replaced with a fresh solution for 2x5 minute washes followed by a 5 minute wash in 5% acetic acid. Gels were stored in $H_2O$ and photographed using Ektachrome ASA 100 film. For standard 5% and 15% separating gels, apparent molecular weights of the protein samples were calculated from plots of the log of the standards molecular weights versus their distance of migration into the gel.

Western blot analysis using alkaline phosphatase conjugated goat anti-mouse IgG (Sigma Chemical Co., St. Louis, Mo.) and a detection kit obtained from Bio-Rad Laboratories was used to confirm the presence of TXU-7 MoAb. This kit is able to detect 10 ng of MoAb protein which has been electrophoretically transferred to a nitrocellulose membrane, following SDS-PAGE, using a semi-dry Semi-Phor apparatus (Model TE-70 Hoefer Scientific, San Francisco, Calif.). In brief, 25 ng of purified Tx-U-7 MoAb and 10 μg of pertained molecular weight standards (Amersham Corp., Arlington fits, Ill.) were boiled in 62.5 mM Tris pH 6.8 containing 1% SDS, 4% glycerol and 0.025% bromophenol blue for 3 minutes and run on a 5% acrylarnide mini-gel (Mini-Protean II, Bio-Rad Laboratories, Hercules, Calif.). Laemmli, cited supra. Electrophoretic transfer of proteins from gels to nitrocellulose membranes was carried out according to the method described by Towbin et. al. with slight modifications. Towbin et al., *PNAS USA*, 76, 4350 (1979).

Following electrophoresis, gels, nitrocellulose membranes (0.4 μm pore size, Bio-Rad Laboratories) and filter paper (3 mm Whatman, Hillsboro, Oreg.) were equilibrated in transfer buffer (25 mM Tris, 192 mM glycine, pH 8.3, 0.01% (w/v) SDS and 10% (v/v) methanol) for 5 minutes. A "sandwich" was prepared with the nitrocellulose membrane placed against the gel on the side of the gel facing the anode and surrounded on each side by 3 pieces of buffer-soaked filter paper. This sandwich was placed into a Hoefer TE-70 semi-dry transfer unit (Hoefer Scientific Instruments, San Francisco, Calif.) and a current of 70–100 mAmps was applied for 30 minutes. After transfer, gels were stained in Coomassie Blue G-250 to examine transfer efficiency. The nitrocellulose membranes were stored in Tris-buffered saline (TBS, 20 mM Tris, 500 mM NaCl, pH 7.5) overnight at room temperature.

One step immunoblotting was done at room temperature using an Immun-Blot Assay kit (Bio-Rad Laboratories) as follows: background sites on the nitrocellulose membranes were blocked by placing the membranes in TBS containing a 3% gelatin (EIA grade, Bio-Rad Laboratories) for 2 hours while gently shaking on a platform rocker (Hoefer Scientific). After decanting the blocking solution, the membranes were washed with 10 mL Tris buffered saline containing Tween-20 (1ITBS, 20 mM Tris, 500 mM NaCl, 0.05% Tween-20, pH 7.5) while gently rocking for 10 minutes. The membranes were incubated in 10 mL of a 3000 fold dilution of the alkaline phosphatase conjugated goat anti-mouse IgG (Sigma Chemical Co.) for 2 hours while gently rocking. The membranes were again washed twice with TTBS and once with TBS, followed by a 10–20 minute incubation in alkaline phosphatase substrate solution containing p-nitroblue tetrazolium chloride and 5-bromo4-chloro-3 indolyphosphate (Bio-Rad Laboratories). The reaction was terminated by washing the membranes twice in 10 mL distilled $H_2O$ for 5 minutes followed by drying the membranes between two pieces of filter paper.

The individual batches of purified TXU-7 MoAb that were combined to form the Lot. The final TXU-7 MoAb preparation (Lot #A-1993) used in generating the clinical TXU-7-PAP immunotoxin was greater than 99% pure. In addition, Western blot analysis using a goat-anti-mouse IgG-alkaline phosphatase conjugate demonstrated that there were no other proteins that were cross-reactive with the anti-mouse antibody.

C. Quality Control Testing and Pre-Clinical Studies on TXU-7 Monoclonal Antibody A manufacturer's working cell bank (MWCB) was established from the master cell bank (MCB) of the TXU-7 MoAb-producing hybridoma cell line. The MCB, as well as the purified TXU-7 MoAb, was sent to Microbiological Associates, Inc. (Rockville, Md.) to be screened for microbial contaminants including bacteria and fungi. In addition, the MCB was tested for the presence of agar-cultivable and noncultivable mycoplasma and for murine viruses (MAP Test) according to the OBRR-FDA "Points to Consider in the Manufacture and Testing of Monoclonal Antibody Products for Human Use." The TXU-7-producing MCB was also assayed for cytopathic effects and hemagglutination due to the presence of adventitious viruses.

A ten-fold concentrated TXU-7 MoAb-containing harvest (before purification) was analyzed for viral particles by electron microscopy. The ability of the antibody purification process to remove/inactivate viruses was assessed by spiking a similar concentrated harvest with high titer Moloney Murine Leukemia virus (MoMLV) and assaying purified samples for infectious virus using the XC Plaque assay. Furthermore, a sample of purified TXU-7 MoAb Lot #A-1993 was sent to Tektagen, Inc. (Malvern, Pa.) for the detection of residual MoMLV. Table 2, below, summarizes the quality control analysis data on purified TXU-7.

TABLE 2

QUALITY CONTROL ANALYSIS OF PURIFIED TXU-7 MONOCLONAL ANTIBODY

| Test Parameters | Results |
| --- | --- |
| Purity | |
| SDS-PAGE | 99.0% |
| HPLC | 99.0% |
| Molecular Weight | |
| Unreduced | 150 kDa |
| Reduced | |
| Immunoreactivity Profile | (+) Molt 3, Jurkatt/T-Lineage ALL |
| (FACS Analysis) | (−) NALM6/B-ALL |
| Endotoxin Contamination (LAL Assay) | 4 EU/mg |
| Rabbit Pyrogen Test | Negative |
| Mouse DNA Contamination (Slot Blot Hybridization Assay) | 171 pg Murine DNA/0.5 mg |
| Sterility Test Direct inoculation method | Negative |
| General Safety Test | Satisfactory (mice and guinea pigs) |
| Acute Toxicity in Mice | $LD_{50}$ (i.v.) > 10,000 µg/mouse |

D. Immunoreactivity Studies on TXU-7 Monoclonal Antibody

The binding of purified TXU-7 MoAb to target cells was determined by standard indirect immunofluorescence (IF). Briefly, $10^6$ cells in 0.1 mL PBS, 2.5% calf bovine serum (CBS) were incubated with various concentrations of monoclonal antibody for 30 minutes at 4° C. After incubation, cells were washed and incubated 30 minutes with 10 µL of a stock solution of FITC conjugated goat anti-mouse IgG (Becton Dickinson, Mountain View, Cailf.) or 50 µL of a 1:20 dilution of FITC conjugated goat F(ab')$_2$ anti-mouse IgG (FITC-GAMG, Cappel Laboratories, Cochranville, N.C.). Cells were then washed three times, resuspended in 200 µL PBS, 2.5% CBS, NaN$_3$, and analyzed using a FACS 440 or Fac Star Plus multiparameter flow cytometer (Becton Dickinson, Mountain View, Calif.).

In cross-competition experiments, which were designed to confirm the specificity of TXU-7 for the CD7 antigen, cells were first preincubated with 100 µg/mL unconjugated TXU-7, or a 1:100 dilution of ascites fluid containing TXU-7 MoAb, for 30 minutes on ice before Leu5(anti-CD2)-FITC, Leu4(anti-CD3)-PE, 10.2(anti-CD5)-PE, G3.7 (anti-CD7)-PE, or Leu9(anti-CD7)-FITC were added at 1 µg/mL to detect remaining free CD7 antibody binding sites. After a 30 minute incubation on ice, the cells were washed three times and analyzed on the FACS 440. MoAb G3.7-PE and Leu9-FITC (anti-CD7) are used as control antibodies. An argon laser (400 MW, 488 nm) was used for excitation of FITC and PE. Fluorescence emissions for FITC and PE were detected by selectively collecting 530±15 nm for FITC and 575±12.5 for PE. Low-angle forward-light scatter and green fluorescence data were scored in the list mode for reanalysis by a Consort 40 PDP/11 computer system (Becton Dickinson, FACS Division, Sunnyvale, Calif.). During analysis of the list mode data files, lymphoid cells were discriminated from monocytes, granulocytes, and dead cells by their characteristic low-angle forward-light scatter and right-angle light scatter properties.

EXAMPLE 3

TXU-7-PAP

A. Large Scale Production and Purification of TXU-7-PAP Immunotoxin

Highly purified preparations of TXU-7 MoAb and PAP (as prepared above in Examples 1 and 2) were used as the starting materials for the large scale preparation of TXU-7-PAP immunotoxin. All column eluants were tested for sterility and the presence of endotoxin (using the Limulus amebocyte assay) prior to use. All of the following steps in the preparation and purification of TXU-7-PAP immunotoxin were performed in the "PAP-MoAb Conjugation Facility" of the Biotherapy Program at the University of Minnesota under GLP conditions using sterile, endotoxin-free buffers and equipment.

1. Modification of TXU-7 MoAb and PAP

PAP toxin and TXU-7 MoAb were modified via their free amino groups prior to the intermolecular conjugation reaction. 2-iminothiolane was used to introduce reactive sulfhydryl groups into PAP and N-succinimidyl 3-(2-pyridyldithio) propionate (SPDP) was used to introduce 2-pyridyl disulfide bonds into TXU-7 MoAb. In brief, 70–100 mg amounts of purified TXU-7 MoAb, at a concentration of 9–14 mg/mL in 40 mM sodium phosphate, 150 mM sodium chloride, pH 7.5 (PBS) were reacted with a 3.5:1 molar excess of SPDP (N-succinimidyl 3-(2-pyridyldithio) propionate; Pharmacia Biotech, Piscataway, N.J.), freshly prepared in DMSO (Hybri-Max grade, Sigma Chemical Co., St. Louis, Mo.), at a concentration of 64 mM, and diluted 1:10 in PBS just prior to use. 50–75 mg amounts of purified PAP, at a concentration of 10–13 mg/mL in PBS, pH 8, were mixed with a 3.5-fold molar excess of 2-iminothiolane HCl (Pierce Chemical Co., Rockford, Ill.), prepared immediately prior to use as a 20 mM solution in 50 mM sodium phosphate, pH 8.6. Both modification reactions were allowed to proceed for 2 hours at room temperature with gentle rocking in sterile endotoxin-free vials (Bayer, Spokane, Wash.).

Excess reagents and low molecular weight reaction products were subsequently removed by gel filtration on Sephadex G-25 PD-10 prepacked columns (Pharmacia Biotech) equilibrated in sterile, endotoxin-free PBS, pH 7.5. Individual fractions were collected and dilutions made in PBS for monitoring at 280 nm. Those containing the majority of the protein were combined and the total amounts of antibody and PAP calculated using E_EQ/S(1%, 280) values of 1.40 and 0.83 for TXU-7 and PAP, respectively. The amount of PAP recovered after this gel filtration step represented 91% (mean+SE=91+1.3%) of the initial amount of the PAP protein subjected to modification. The amount of TXU-7 MoAb recovered after gel filtration represented 86% (mean+SE=86+3.6%) of the initial amount of the TXU-7 MoAb protein subjected to modification.

2. Conjugation of TXU-7 MoAb and PAP

Modified PAP toxin was reacted with modified TXU-7 MoAb resulting in a sulfhydryl-disulfide exchange reaction and yielding a disulfide linked PAP-TXU-7 MoAb conjugate, which is referred to herein as TXU-7-PAP immunotoxin. Specifically, 2-iminothiolane-derivatized PAP was added to the SPDP-modified TXU-7 MoAb at a final molar ratio of 3.5:1, PAP-TXU-7 MoAb. This mixture was incubated for 2 hours in sterile, endotoxin-free vials at room temperature with gentle rocking and left at 4° C. overnight Gentle rocking was continued for 4–5 hours the following day before the reaction mixture was filtered (0.2 μm Acrodisc, Gelman Sciences, Ann Arbor, Mich.) in preparation for the HPLC step.

SDS-PAGE analysis of samples from the conjugation mixture was routinely used to monitor the conjugation efficiency. The relative amounts of distinct protein species were determined by gel scanning, as described above. In each conjugation, this analysis revealed the presence of a significant amount of unreacted PAP and a number of distinct TXU-7-PAP immunotoxin species which differed in their relative molecular weights. Two major TXU-7-PAP immunotoxin bands corresponding to apparent molecular weights of 180 kDa and 210 kDa were consistently found, consistent with the presence of 1 or 2 PAP molecules linked to each TXU-7 MoAb molecule. In addition, a TXU-7-PAP immunotoxin species was found that corresponded to an apparent molecular weight of 240 kDa, consistent with the presence of 3 PAP molecules linked to each TXU-7 MoAb molecule, as well as very large immunotoxin species corresponding to molecular weights in excess of 300 kDa. The presence of TXU-7 MoAb, as well as PAP toxin moieties, in the immunotoxin species, was confirmed by immunoblotting using anti-PAP and anti-mouse IgG antibodies.

3. Purification of TXU-7-PAP Immunotoxin

The TXU-7/PAP reaction mixture was subjected to gel filtration chromatography by HPLC (utilizing a 21.5×600 mm Spherogel TSK3000SW column, TosoHaas and Beckman Instruments) to remove unreacted PAP as well as high molecular weight (≧300 kDa) aggregates. Although the column has a theoretical maximum sample load of 200 mg of protein and a maximum sample volume of 5 mL, a maximum of 50 mg of the conjugation mixture was injected in order to minimize aggregate formation which occurs at higher protein concentrations. The column was equilibrated in 100 mM sodium phosphate buffer, pH 6.8, at a flow rate of 3 mL/minute. The large immunotoxin species began to elute from the 21.5×600 mm TSK 3000SW column at 14 minutes post-injection, followed by the 240 kDa, 210 kDa, and 180 kDa immunotoxin species and unconjugated MoAb at 21–34 minutes. Unreacted PAP elutes at 50–55 minutes and was well separated from the TXU-7-PAP conjugates.

One hundred mg batches of the semipurified TXU-7-PAP immunotoxin from the HPLC step were then concentrated to a volume of 15–20 mL using Centriprep-30 devices (Amicon, Beverly, Mass.). N-ethylmaleimide (Sigma), freshly prepared in DMSO and diluted in PBS to give a final solution of 8 mM, was added to the concentrated TXU-7-PAP in a 10:1 molar ratio and gently rotated at room temperature for 15 minutes in a 50 mL centrifuge tube before being dialyzed against 10 mM sodium phosphate buffer, pH 7.1, using Spectra/Por2 dialysis tubing.

Ion exchange chromatography on CM-Sepharose Fast Flow resin (Sigma Chemical Company, St. Louis, Mo.) was used to further purify TXU-7-PAP immunotoxin from any remaining unconjugated TXU-7 MoAb. Briefly, the column was equilibrated in 10 mM sodium phosphate buffer, pH 6.5, and the pH and conductivity of the effluent were measured. After overnight dialysis at 4° C., the sample was adjusted to the pH and conductivity of the column. The sample was then applied to the column under conditions of low ionic strength and pH (10 mM sodium phosphate, pH 6.5) and all species of immunotoxin as well as the TXU-7 MoAb bound to the resin. TXU-7 MoAb was then eluted with 10 mM sodium phosphate, pH 7.8, containing 20 mM sodium chloride.

When the TXU-7-PAP had completely drained into the resin, the column was washed briefly with 10 mM sodium phosphate buffer, pH 7.1, and the unconjugated antibody eluted with 10 mM sodium phosphate, pH 7.8, containing 20 mM sodium chloride. When the peak of TXU-7 MoAb had come through and the absorbance at 280 nm had returned to baseline, the TXU-7-PAP immunotoxin was eluted from the CM-Sepharose using 40 mM sodium phosphate buffer, pH 7.5, containing 150 mM sodium chloride (PBS). The immunotoxin peak was collected in 4 mL fractions which were subsequently combined, following SDS-PAGE analysis to verify the absence of unconjugated TXU-7 MoAb and the presence of immunotoxin species of approximately 180 kDa, 210 kDa, and 240 kDa (i.e., containing one, two, or three PAP molecules bound to each antibody molecule).

Protein concentrations were determined for the TXU-7-PAP immunotoxin using the Bicinchoninic Acid Protein Assay kit obtained from Sigma Chemical Company. Bicinchoninic acid is a chromogenic reagent, highly specific for Cu(I), which forms a purple complex with an absorbance at 562 nm that is directly proportional to the protein concentration. Individual batches of CM-Sepharose purified TXU-7-PAP immunotoxin were tested for their potency using in vitro cytotoxicity assays and for their endotoxin levels. If further treatment was required to remove endotoxin, the TXU-7-PAP was concentrated to 2.5 mg/mL using Centriprep-30 devices (Amicon) and mixed with Affi-Prep Polymyxin resin (Bio-Rad Laboratories) before being filter-sterilized. The yield of the final CM-Sepharose purified immunotoxin product was 11.5% of the amount of the TXU-7 MoAb initially used in the conjugations.

4. Endotoxin Removal

The Affi-Prep Polymyxin Support (obtained from Bio-Rad Laboratories, Hercules, Calif.) was used to remove endotoxin from the purified TXU-7-PAP immunotoxin preparations. Myers et al., *J. Immunol. Methods*, 136, 221 (1991). The resin was washed 5 times with sterile, endotoxin free $H_2O$, treated with 0.1 N NaOH for 30 minutes at room temperature with gentle rocking, followed by washing 5 times with sterile, endotoxin-free 40 mM sodium phosphate buffer, pH 7.5, containing 150 mM sodium chloride. Finally, the resin was washed 5 times with 10 mM sodium phosphate buffer, pH 6.4, to bring the pH down to 7.0. Ten mL of TXU-7-PAP, at a concentration of 2.5 mg/mL, were then added to 12 mL of washed Affi-Prep Polymyxin resin in a sterile and pyrogen-free 50 mL centrifuge tube. The mixture was gently rotated overnight at 4° C. (24–36 hrs), and the resin was allowed to settle. The immunotoxin-containing supernatant was carefully removed and sterile-filtered into a sterile, endotoxin-free class vial. Five mL amounts of sterile PBS are added to wash the resin.

This supernatant was filtered into the same glass vial and a sample removed for the LAL assay.

Endotoxin contamination of TXU-7-PAP immunotoxin was 3.0 EU/mg as determined by the LAL assay. The estimated highest total TXU-7-PAP dose to be administered in the projected phase I toxicity study is 0.25 mg/kg (0.05 mg/kg/dose×5 doses). Hence, patients would receive 0.75 EU/kg endotoxin at the highest immunotoxin dose.

5. Quality Control Testing and Pre-clinical Studies of TXU-7-PAP Immunotoxin a. SDS-PAGE and Western Blot Analysis For biochemical testing of purity of the TXU-7-PAP immunotoxin, 3.5 µg amounts of CM-Sepharose purified TXU-7-PAP protein were boiled in sample buffer containing 40 mM Tris buffer pH 6.8, 2% SDS, 7.5% glycerol and 0.005% bromophenol blue tracking dye and electrophoresed on 5% separating gels or 4–20% gradient gels (Bio-Rad Laboratories, Hercules, Calif.) as described above for PAP and TXU-7 MoAb. Laemmli, cited supra.

Furthermore, the presence of the PAP and TXU-7 moieties in purified TXU-7-PAP immunotoxin was confirmed using Western blot analysis and a detection kit obtained from Bio-Rad Laboratories. This kit contains a goat-anti-rabbit IgG-alkaline phosphatase conjugate and is able to detect 10 ng of PAP protein which has been electrophoretically transferred to a nitrocellulose membrane, following SDS-PAGE, using a semi-dry Semi-Phor apparatus (Model TE-70 Hoefer Scientific, San Francisco, Calif.). This method was also used to verify the removal of unconjugated PAP from the clinical preparations of TXU-7-PAP immunotoxin. In brief, 100 ng of purified TXU-7-PAP (1 mg/mL concentration), 10 ng of purified PAP and 10 mg of prestained molecular weight standards were boiled in 62.5 mM Tris pH 6.8 containing 1% SDS, 4% glycerol and 0.025% bromophenol blue for 3 minutes and run on a 15% acrylamide mini-gel (Mini-Protean II, Bio-Rad Laboratories, Hercules, Calif.). Laemmli, cited supra. Electrophoretic transfer of proteins from gels to nitrocellulose membranes was carried out according to the method described by Towbin with slight modifications. Towbin et al., cited supra.

After transfer, gels were stained in Coomassie Blue R-250 to examine transfer efficiency and nitrocellulose membranes were stored in Tris-buffered saline (TBS, 20 mM Tris, 500 mM NaCl, pH 7.5) overnight at room temperature. Two step immunoblotting was done at room temperature using an Immun-Blot Assay kit (Bio-Rad Laboratories) as follows: background sites on the nitrocellulose membranes were blocked by placing the membranes in TBS containing 3% gelatin (EIA grade, Bio-Rad Laboratories) for 2 hours while gently shaking on a platform rocker (Hoefer Scientific). After decanting the blocking solution, the membranes were washed with 10 ML Tris buffered saline containing Tween-20 (TTBS, 20 mM Tris, 500 mM NaCl, 0.05% Tween-20, pH 7.5) while gently rocking for 10 minutes. The membranes were incubated in 10 mL of primary antibody solution (rabbit anti-PAP, RVF UM-1, 10.7 mg/mL diluted 1/500 in TTBS containing 1% gelatin) for 2 hours while gently rocking. The anti-PAP primary antibody was generated in rabbits that had been hyperimmunized with purified PAP.

Following two washes in TTBS to remove any unbound primary antibody, the membranes were incubated in 10 mL of a 3000-fold dilution of the secondary antibody (goat anti-rabbit IgG (H+L) alkaline phosphatase conjugate (Bio-Rad Laboratories) for 2 hours with gentle rocking. The membranes were again washed twice with TTBS and once with TBS, followed by a 10–20 minute incubation in alkaline phosphatase substrate solution containing p-nitroblue tetrazolium chloride and 5-bromo-4 chloro-3 indolylphosphate (Bio-Rad Laboratories). The reaction was terminated by washing the membranes twice in 10 mL distilled $H_2O$ for 5 minutes followed by drying the membranes between two pieces of filter paper. Similarly, single step immunoblotting using purified TXU-7 MoAb as a standard was done using alkaline phosphatase conjugated goat anti-mouse IgG (Sigma Chemical Co., St. Louis, Mo.) to detect unconjugated TXU-7 MoAb remaining in the immunotoxin preparations.

SDS-PAGE with gel scanning, and Western blot analyses using anti-PAP or anti-mouse IgO antibodies indicated that the final product (Lot #I-1994) contained 39% 210 kDa TXU-7-PAP, 42% 180 kDa TXU-7-PAP, 12.5% free TXU-7 MoAb and 5.5% free PAP.

The purified TXU-7-PAP immunotoxin dissociates into its homogeneous IgG heavy chain, kappa light chain, and PAP toxin components after reduction, providing further corroborative evidence for the purity of TXU-7-PAP immunotoxin.

EXAMPLE 4

Immunoreactivity of TXU-7-PAP

The ability of TXU-7-PAP to bind to leukemic blasts was determined by a double sandwich method in which the cells are incubated in a sequential fashion with (a) 10 mg/mL immunotoxin (IT) (50 nM, 30 minutes, 4° C.), (b) affinity-purified rabbit anti-PAP IgG-PE conjugate (1:20 dilution, 15 minutes, 4° C.), and (c) FITC-conjugated goat anti-mouse IgG (Becton Dickinson, Mountain View, Calif.) (1:20 dilution, 15 minutes, 4° C.). Cells were analyzed by cytofluorometry using a FACS IV (Becton Dickinson Immunocytochemistry Systems, Mountain View, Calif.).

Bone marrow blasts from T-lineage ALL patients were examined for the presence of bound immunotoxin after treatment with 10 mg/mL (50 nM) TXU-7-PAP. T-lineage ALL cells reacted with the TXU-7-PAP immunotoxin in all cases studied. In contrast, these blasts did not bind control immunotoxin B43-PAP, which is directed against B-lineage-associated surface determinants. These results demonstrated that the MoAb moiety of TXU-7-PAP immunotoxin retained its specificity and affinity for the target CD7 antigen. Hence, the conjugation procedure did not specifically alter the immunoreactivity of TXU-7 MoAb.

Serial dilution clonogenic assays were performed to determine the log kill efficacy of TXU-PAP immunotoxin against clonogenic cells from the T-lineage ALL cell line Molt-3, and the control NALM-6 (B-ALL) and HL-60 (AML) cell lines. The inhibition of the clonogenic growth of leukemic cells following immunotoxin treatment was evaluated by a quantal serial dilution assay. Clonogenic growth in wells was examined by using an inverted phase microscope after 14 days of culture at 37° C. in 5% $CO_2$/95% air in clonogenic medium (RPMI 1640 supplemented with 2.5% calf bovine serum, 2 mM L-glutamine, 1 mm sodium pyruvate, 1% penicillin/streptomycin). The extent of leukemia cell elimination was expressed as log kill=log $\phi$ control/$\phi$ test) where $\phi$ is the most probable number of clonogenic units (CU) as estimated by the Spearman Kaerber method.

Target cells ($10^6$–$10^7$/mL) were treated with TXU-PAP in IMDM+2% HSA at pH 7.5 for 2 hours on ice followed by 2 hours (short term) or 16 hours (long term) in a humidified atmosphere at 37° C. and 5% $CO_2$/95% air. Controls were (a) untreated cultures and (b) nontarget leukemic cells that were sensitive to PAP. After treatment, cells were washed with aMEM medium to remove unbound immunotoxin.

TXU MoAb stained 96% of CD7 antigen positive Jurkat T-lineage leukemia cells and 99% of CD7 antigen positive MOLT-3 T-lineage leukemia cells under conditions where less than 1% of CD7 antigen negative NALM-6 pre-B leukemia cells were stained.

MOLT-3 T-lineage leukemia cells were examined for the presence of bound immunotoxin after treatment with 0.1 µg/mL, 1.0 µg/mL or 10 µg/mL (50 nM) TXU-PAP by indirect immunofluorescence using FITC-conjugated goat anti-mouse IgG as a probe. The percentage of immunofluorescent MOLT-3 cells increased after treatment with TXU-PAP in a dose-dependent fashion. At the highest concentration, 98% of MOLT-3 cells were positive for cell-surface bound TXU-PAP. By comparison, only 8% NALM-6 cells showed above background fluorescence after treatment with the highest concentration of TXU-PAP. These results demonstrated that the MoAb moiety of TXU-PAP immunotoxin retained its specificity and affinity for the target CD7 antigen.

In serial dilution clonogenic assays, anti-CD7 (TXU)-PAP was very effective against clonogenic blasts from the CD7 antigen positive T lineage leukemia cell line, MOLT 3, and killed 2.8–3.7 logs at 1 µg/mL (=5 nM). By comparison, only 0.7 log of NALM-6 or HL-60 cells were inhibited in their clonogenic growth. Furthermore, in leukemic progenitor cell assays, TXU-PAP killed primary clonogenic leukemic cells from T-lineage ALL patients regardless of the level of radiation resistance.

EXAMPLE 5

In vivo Toxicity Studies

A. Toxicity of Pokeweed Antiviral Protein (PAP)

Female BALB/c mice weighing approximately 20 grams were given a single intravenous injection of purified PAP (Lot #P-1993) via the tail vein. Eight different doses were used ranging from 10 µg to 175 µg and each dose was tested in 5 mice. Mice were monitored for 30 days for morbidity and mortality. No deaths were observed with doses as high as 100 g/20 g mouse or 5 g/g (=3.1 $g/cm^2$=5 mg/kg). This non-toxic dose is >90-fold higher than the highest PAP dose that will be given to patients as a TXU-7 antibody conjugate. Deaths were observed only in the groups receiving 150 µg/20 g mouse (=7.5 mg/kg) or higher doses. A dose of 150 µg/20 g mouse is >60-fold higher than the highest PAP dose that will be given to patients as the TXU-7-PAP immunotoxin.

B. Toxicity of AU-7-PAP Immunotoxin

The toxicity of TXU-7-PAP immunotoxin was analyzed in a total of 4 studies. All slides (formalin-fixed) were evaluated by a senior veterinary pathologist of the Division of Comparative Medicine, Department of Laboratory Medicine and Pathology at the University of Minnesota.

In the first and fourth studies, groups of 5 female BALB/c mice weighing approximately 20 grams were given a single intravenous or intraperitoneal injection of TXU-7-PAP immunotoxin in 5 different doses ranging from 10 µg/mouse to 100 µg/mouse. In the second and third studies, mice received three consecutive intravenous doses. No sedation or anesthesia was used in an attempt not to obscure the toxicity information.

In the first study, groups of 5 female BALB/c mice, each weighing 19–26 grams, received via the tail vein a single intravenous bolus injection of TXU-7-PAP immunotoxin in 0.2 mL volume in doses ranging from 10 µg/mouse to 100 µg/mouse. Mice were monitored for mortality for determination of the day 30 $LD_{50}$ values and multiple organs were collected within 4 hours after death, grossly examined, and fixed in formalin Slides were prepared for histopathologic examination. Mice surviving at 30 days post treatment were sacrificed and multiple organs were immediately collected from randomly selected, 2 mice/dose group, and preserved in 10% buffered formalin for preparation of slides and histopathologic examination.

At 50 µg and higher doses, the clinical signs of TXU-7-PAP toxicity included weight loss, weakness, scruffy skin, decreased activity, lethargy, and gait disturbances. Deaths were observed as late as 16 days post TXU-7-PAP treatment. $LD_{50}$ values are expressed as day 30 $LD_{50}$ (Most groups report day 7 $LD_{50}$). The day 30 $LD_{50}$ was 50 µg/20 g, mouse (=2.5 µg/g or 1.55 µg/$cm^2$=2.5 mg/kg). At this dose level, some mice were alive after 14 and 30 days, respectively, with a median survival time of greater than 30 days.

Since 50 µg of TXU-7-PAP contains approximately 8.0 µg of PAP, these findings demonstrate that conjugated PAP is approximately 20-fold more toxic than unconjugated PAP, probably in part because of prolonged half-life and in part because of Fc-receptor mediated non-specific binding of the immunotoxin to tissues which would otherwise not be affected by PAP.

EXAMPLE 6

In Vivo Stability of TXU-7-PAP Immunotoxin

To determine the in vivo stability of TXU-7-PAP immunotoxin of the present invention, New Zealand white female rabbits weighing 3 kg are injected intravenously with a 1 mg dose of TXU-7-PAP or free antibody alone. Peripheral blood is obtained by retroorbital venipuncture at multiple time points following the administration of the immunotoxin and serum concentrations of intact immunotoxin as well as unconjugated antibody are determined by solid phase ELISA, as previously described (Uckun et al., *Leukemia and Lymphoma*, 9, 459 (1993); and Myers et al., *Leukemia and Lymphoma*, 18, 93 (1995)). Two separate but linked two-compartment first-order pharmacokinetic models, one for the intact immunotoxin and one for free antibody data are fit simultaneously to the intact immunotoxin and free antibody data within the same animal. Maximum likelihood estimation, as implemented in ADAPT-II Software, is used to determine the pharmacokinetic parameters. In contrast to the PAP immunotoxins disclosed in the U.S. patent application Ser. No. 07/979,470, the disclosure of which is incorporated by reference herein, which displayed very poor in vivo stability, the immunotoxin of the present invention exhibits in vivo stability, as measured by longer serum half-life and greater systemic exposure (i.e., area under concentration-time curve).

EXAMPLE 7

In Vivo Anti-Leukemic Activity

Female SCID mice were inoculated i.v. with $10 \times 10^6$ MOLT-3 cells, immediately followed by one of the following i.p. treatments for 3 consecutive days: PBS (n=10), 30 $\mu$g of B43(anti-CD19)PAP (10 $\mu$g/day×3 days; n=6), 30 $\mu$g of TXU(anti-CD7) antibody (10 $\mu$g/day×3 days; n=3) 15 $\mu$g/mouse TXU(anti-CD7)PAP (5 $\mu$g/day×3 days; n=10), or 30 $\mu$g/mouse TXU(anti-CD7)-PAP (5 $\mu$g/day×3 days; n=10). In the control group of 19 mice (i.e., mice treated with TXU antibody, B43-PAP or PBS), only 21±9% of mice remained alive for $\geq$60 days, with a median survival of 37 days, and none survived beyond 80 days. In contrast, 80±13% of mice in the, 15 $\mu$g/mouse (0.25 mg/kg/day×3 days) TXU(anti-CD7)-PAP treatment group remained alive at 120 days post-treatment, with a median survival of 116.4 days. In the 30 $\mu$g/mouse (0.50 mg/kg/day×3 days) TXU(anti-CD7)-PAP group, all of the mice remained alive for $\geq$120 days. These differences in survival outcome were statistically significant (control versus 15 $\mu$g of TXU-PAP, P<0.0001 by log-rank test; control versus 30 g of TXU-PAP, P<0.000001 by log-rank test).

Thus, TXU-PAP elicited a potent antileukemic activity in SCID mice challenged with an otherwise invariably fatal human CD7+ T-lineage ALL. Although all 19 control mice died within 80 days after inoculation of leukemia cells, 80% of the mice in the 15 $\mu$g/mouse (0.75 mg/kg) TXU-PAP treatment group and 100% of the mice in the 30 $\mu$g/mouse (1.50 mg/kg) TXU-PAP treatment group remained alive at 120 days post-treatment.

EXAMPLE 8

TXU-7-PAP as an Antiviral Therapeutic Agent
Materials and Methods

Preparation of PAP Immunotoxins. Controls included unconjugated PAP, B43(anti-CD19)-PAP directed against B-cells, and unconjugated mAb B53(anti-CD4) and TXU (anti-CD7). These control reagents were prepared as described above. Additional controls included AZT and 2',3'-didehydro-2', 3'-dideoxythymidine (d4T).

Stock $HTLV_{IIIB}$ Virus. The HIV-1 strain $HTLV_{IIIB}$, which was propagated in CCRF-CEM cells, was used in in vitro assays of the anti-HIV-1 activity of PAP immunoconjugates. Cell-free supernatants of $HTLV_{IIIB}$-infected CCRF-CEM cells were harvested, dispensed into 1 ml aliquots, and frozen at $-70°$ C. Periodic titration of stock virus was performed by examining its cytopathic effects in MT-2 cells.

In Vitro Assays of Anti-HIV-1 Activity. Normal human peripheral blood mononuclear cells (PBMNC) from HIV-negative donors were cultured 72 hours in RPMI 1640 supplemented with 20% (v/v) heat-inactivated fetal bovine serum (FBS), 3% interleukin-2, 2 mM L-glutamine, 25 mM HEPES, 2 gL $NaHCO_3$, 50 $\mu$g/ml gentamicin, and 4 $\mu$g/ml phytohemagglutinin prior to exposure to HIV-1 at a multiplicity of infection (MOI) of 0.1 during a one-hour adsorption period at 37° C. in a humidified 5% $CO_2$ atmosphere. Subsequently, cells were cultured in 96-well microliter plates (100 $\mu$l/well; $2 \times 10^6$ cells/ml) in the presence of various concentrations of PAP immunoconjugates or standard anti-HIV drugs and aliquots of culture supernatants were removed from the wells on the seventh day after infection for p24 antigen and reverse transcriptase (RT) assays. The p24 enzyme immunoassay (EIA) employed was the unmodified kinetic assay commercially available from Coulter Corporation Immunotech, Inc. (Westbrooke, Me.), which utilizes a murine mAb to HIV core protein coated onto microwell strips to which the antigen present in the test culture supernatant samples binds. Percent viral inhibition was calculated by comparing the p24 values from the test substance-treated infected cells with p24 values from untreated infected cells (i.e., virus controls).

To assess RT activity, a procedure commercially available from Amersham Lifescience, which employs a DNA/RNA primer/template attached to scintillant-filled fluomicrospheres, was employed. Incorporation of radiolabeled nucleotides by reverse transcription results in extension of the primer and stimulation of the scintillant within the microspheres. The resulting signals of RT activity were detected and quantified by a scintillation counter and recorded as counts per minute (cpm). In some experiments, the anti-HIV activity of 1:2, 1:10, 1:20, and 1:100 diluted plasma samples obtained at one hour post-therapy from TXU-PAP-treated cynomolgus monkeys against $HTLV_{IIIB}$ was examined. The intravenous TXU-PAP doses were 50 $\mu$g/kg for monkey 52E and 100 $\mu$g/kg for monkey 52D and monkey 410C. In parallel, the effects of various treatments on cell viability were also examined, as described by Erice et al., supra, and Zarling et al., supra. In brief, non-infected PBMNC were treated with PAP immunoconjugates for 7 days under identical experimental conditions. A microculture Tetrzolium Assay (MTA), using 2,3-bis(2-methoxy4nitro-5-sulfophenyl)-5-[(phenylamino)-carbonyl]-2H-tetraolium hydroxide (XTT), was performed to quantitate cellular proliferation.

Preparation of Viral Stocks of Clinical HIV-1 Isolates. HIV-1 isolates were recovered from peripheral blood specimens of HIV-1 infected patients participating in NIH-sponsored AIDS clinical trials at the University of Minnesota AIDS Clinical Trials Unit (ACTU), using a previously detailed culture technique (Jackson et al., *J. Clin. Micro.*, 28, 16 (1990); Erice et al., *J. Clin. Micro.*, 30, 444 (1992); Levy et al., *J. Infect. Dis.*, 152, 734 (1985)). In brief, $10 \times 10^6$ Ficoll-Hypaque separated mononuclear cells from seropositive patients were co-cultured with $5 \times 10^6$ PHA-stimulated peripheral blood mononuclear cells from an HIV-1 seronegative healthy volunteer donor for 42 days at 37° C./5% $CO_2$ in 50 mL tissue culture flasks containing 15 mL RPMI 1640 supplemented with 20% fetal calf serum, 5% interleukin 2 (Cellular Products, Buffalo, N.Y.), 160 U/mL penicillin, and 160 µg/mL streptomycin. Co-culture supernatants were assayed every 3–4 days for the presence of HIV-1 p24 gag antigen using a commercially available ELISA p24 antigen detection kit (Abbott Laboratories, North Chicago, Ill.). p24 antigen positive cultures were expanded according to a standard protocol and aliquots of cell-free stock viruses were prepared from supernatants of expanded cultures when the reverse transcriptase (RT) activity in the supernatant exceeds 20,000 cpm/50 µL. Some isolates were recovered from frozen supernatants of p24 antigen positive cultures or from frozen cells of HIV-1 culture-positive patients. In these cases, normal donor peripheral blood mononuclear cells ($2-5\times10^6$ cells/mL) were exposed for 2 hours at 37° C./5% $CO_2$ to 1 mL of the p24 positive culture supernatant or $1\times10^6$ thawed peripheral blood mononuclear cells from HIV-1 culture positive patients and cultured in 50 mL tissue culture flasks. Subsequently, positive cultures were expanded as described above.

SCID Mouse Model of Human AIDS. All SCID mice used in the efficacy study were produced by SPF CB-17 scid/scid breeders in the AAALAC-approved and accredited Research Animal Resources (RAR) SCID Mouse Facility of the University of Minnesota (Minneapolis, Minn.). All husbandry and experimental contact made with the mice maintained SPF conditions. The mice were housed in Micro-Isolator cages containing autoclaved food, water and bedding. Trimethoprim/sulfamethoxazole (Bactrim) was added to the drinking water of the mice three times a week. Hu-PBL-SCID mice were generated by reconstituting SCID mice by intraperitoneal injection of $10\times10^6$ peripheral blood mononuclear cells from a single EBV-seronegative volunteer donor. Two weeks after inoculation of cells, mice were challenged by intraperitoneal injection of $1.4-7.7\times10^4$ median tissue culture infectious doses ($TCID_{50}$) of cell free virus. Three different clinical HIV-1 strains (AT-101, AT-328, AT-332) were used. These isolates were recovered from peripheral blood leukocytes of HIV-1 infected individuals participating in National Institutes of Health-sponsored AIDS clinical trials at the University of Minnesota (Jackson et al., supra; Erice et al., supra; Levy et al., supra). SCID mice were infected with HIV-1 isolates in a Biosafety Level 3 containment facility and all manipulations were performed in a biosafety cabinet. In ZDV-treated mice, i.e., AZT, ZDV was added to their water at 1 mg/nl final concentration, resulting in an average consumption of 200 mg/kg/day of ZDV.

Escalating doses of PAP immunotoxins were administered intraperitoneally by injecting half of the total dose as an intraperitoneal bolus dose and delivering the remainder of the total dose over 2 weeks using Alzet micro-osmotic pumps or by administering the total dose by daily intraperitoneal injections over a 5 day treatment period. Throughout the experimental period, mice were monitored daily for overall health and survival. Two weeks after infection with HIV-1, Hu-PBL-SCID mice were electively killed and their peritoneal lavage cells as well as spleen cells were examined for evidence of infection by an HIV-1 culture assay as well as by PCR amplification of a 115 bp DNA sequence in the gag region of the HIV-1 genome, as detailed hereinafter.

For histopathologic studies, tissues were fixed in 10% neutral buffered formalin, dehydrated, and embedded in paraffin by routine methods. Glass slides with affixed 6 micron tissue sections were prepared, stained with H&E, and submitted to the veterinarian pathologist for examination.

Fresh peritoneal lavage cells as well as spleen cells were isolated, co-cultured with phytohemagglutinin (PHA)-stimulated human peripheral blood mononuclear cells from an HIV-1 antibody negative donor, and culture supernatants were tested every 34 days for a maximum of 28 days for the presence of HIV-1 antigen using a commercially available enzyme immunoassay (Abbott Laboratories, North Chicago, Ill.) that detects primarily the core p24 antigen of HIV-1. Goudsmit et al., *J. Infectious Diseases*, 155, 558 (1987).

In addition to the culture method described above, the DNA from the peritoneal lavage cells as well as splenocytes was isolated for detection of HIV-1 DNA by PCR amplification of a 115 bp sequence in the gag region of the HIV-1 genome using two 29-base oligonucleotide primers, SK38 and SK39, that flank the region to be amplified (Ou et al., supra). DNA samples were also examined for the presence of human DNA by PCR amplification of a 110-bp fragment from the first exon of the human beta-globin gene using two 20-base oligonucleotide primers, PCO3 and PCO4, that flank the region to be amplified (Ho et al., NFJM, 317 278 (1987)). Oligonucleotide primers (SK38:5'ATA ATC CAC CTA TCC CAG TAG GAG AAA T3'; SEQ ID NO:1, and SK39: 5'TTT GGT CCT TGT CTT ATG TCC AGA ATG C3'; SEQ ID NO:2) were synthesized by the University of Minnesota Microchemical Facility using an Applied Biosystems Synthesizer (Foster City, Calif.). HIV DNA was amplified using 1.0 µg genomic DNA with 2.5 U of Taq DNA Polymerase (Perkin-Elmer Cetus, Norwalk, Conn) in 1×PCR buffer (50 mM KCl, 10 mM Tris-Cl pH 8.3, 2.5 mM $MgCl_2$ and 0.01% wt/vol gelatin) containing 0.5 µM of each primer and 200 µM dNTP's (Pharmacia, Piscataway, N.J.) in a total volume of 100 µL. Before amplification, samples were overlaid with 100 µL of mineral oil (Sigma, St. Louis, Mo.). Thirty cycles were performed by incubating samples at 95° C. for 1 minute and 60° C. for 1 minute.

Oligomer hybridization was used to detect PCR amplified-HIV DNA. Briefly, 30 µL of amplified DNA was added to 10 µL of probe mixture consisting of 0.2 pmol $^{32}$P-labeled SK19 (5'ATC CTG GGA TTA AAT AAA ATA GTA AGA ATG TAT AGC CCT AC 3'; SEQ ID NO:3), 24 mM NaCl and 4 mM EDTA, pH 8.0. Samples were denatured in a 95° C. bath for 5 minutes followed by a 55° C. 15 minute incubation to anneal probe and target sequences. Ten µL of bromophenol blue/xylene cyanol dye mix was added to each tube and 25 µL of each sample was analyzed on a 10% polyacrylamide gel in 1×TBE buffer (0.089 M Tris-borate and 0.002 M EDTA). Following electrophoresis, the gel was dried and exposed to Kodak XAR-5 film for 2 hours with an intensifying screen.

Results

Figure 1B:
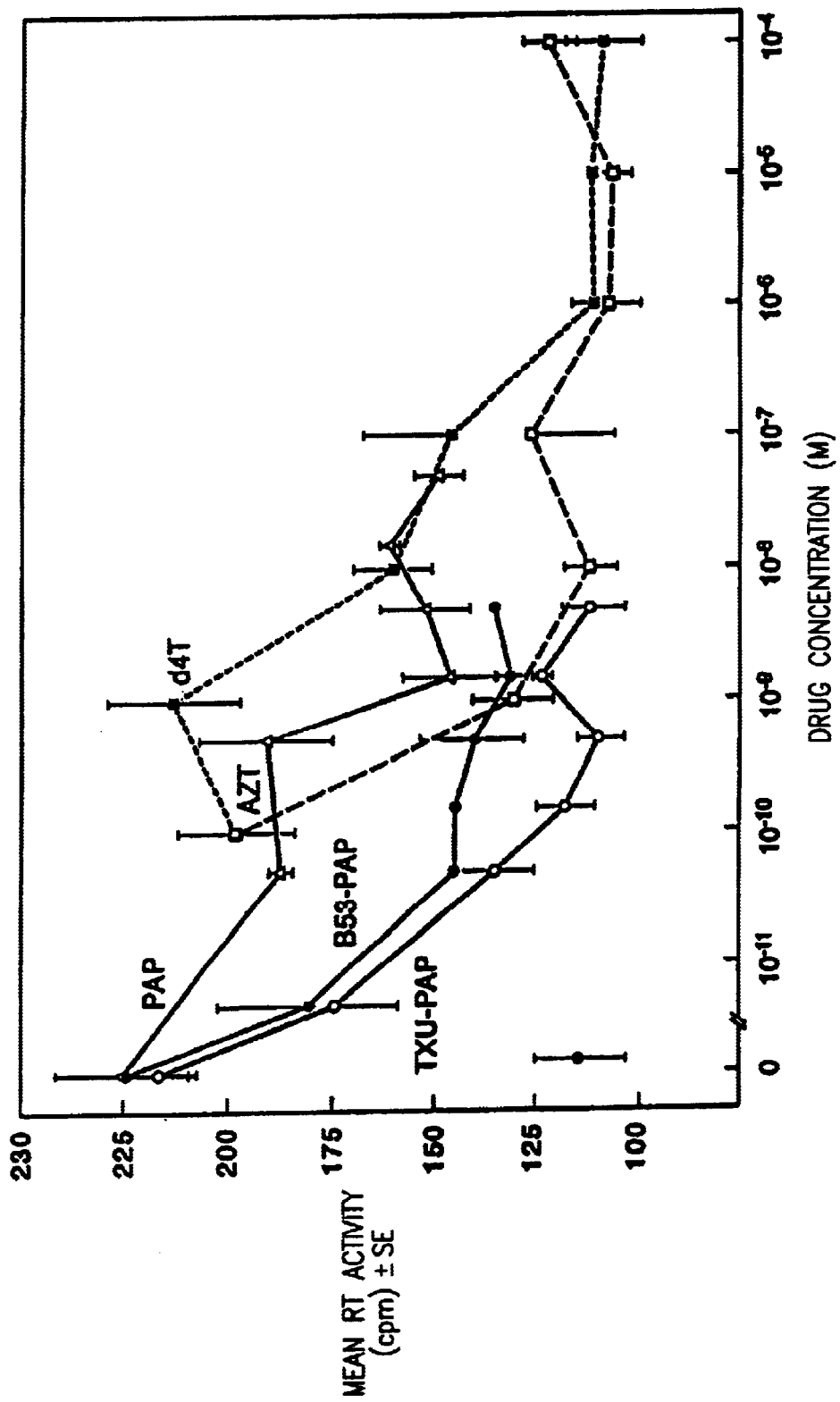

In Vitro Anti-HIV Activity of B53(anti-CD4)-PAP and TXU(Anti-CD7-PAP Immunotoxins. The antiviral activity of PAP immunotoxins against $HTLV_{IIIB}$ was evaluated using HIV-1 p24 core antigen production as a marker of viral replication. As shown in FIG. 1A, both B53-PAP and TXU-PAP inhibited viral replication in a dose-dependent fashion. The $ID_{50}$ values for HIV-1 p24 production were 30 pM (5.9 ng/ml) for B53(anti-CD4)-PAP and 20 pM (4.4 ng/ml) for TXU(anti-CD7)-PAP, whereas unconjugated PAP inhibited p24 production 270- to 400-times less efficiently with an $ID_{50}$ value of 8 nM (228 ng/ml). Both PAP-containing immunotoxins were two-three orders of magnitude more potent than AZT (ZDV) ($ID_{50}$ 1 nM) or 2',3'-didehydro-2', 3'-dideoxythymidine (d4T) ($ID_{50}$=18 nM). A similar efficacy profile was produced when reverse transcriptase activity served as an indicator for viral replication (FIG. 1B). Thus, the antiviral effects of PAP-containing immunoconjugates influence both structural and functional proteins of HIV-1, without eliciting significant cytotoxicity.

Figure 2A:
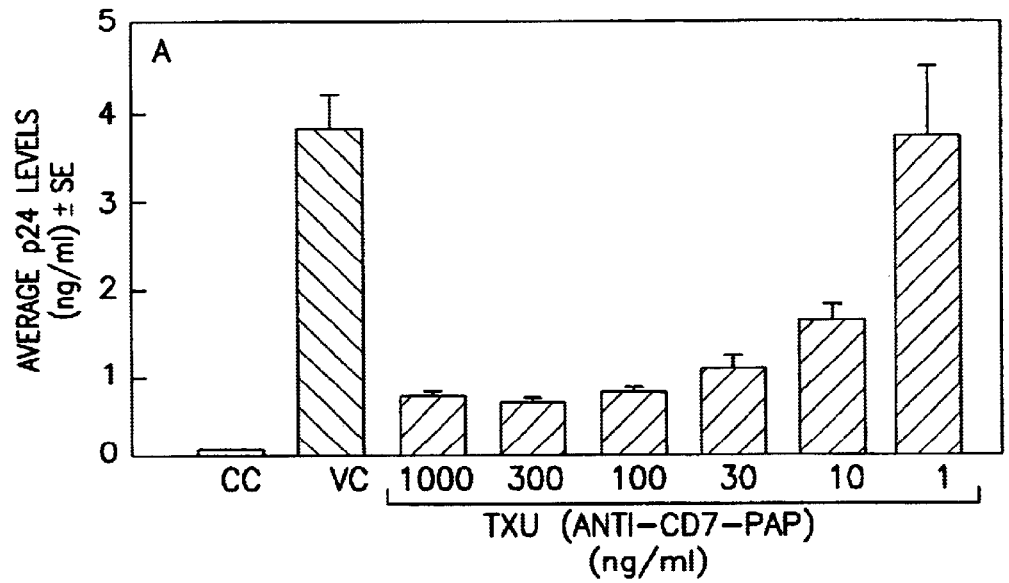
FIG. 2. TXU(anti-CD7)-PAP is a potent and nontoxic inhibitor of HIV-1 in vitro. TXU-PAP inhibited HIV-1 replication, as measured by p24 production (panel A) and RT activity (panel B), in a dose-dependent fashion and without cytotoxicity to the cells (panel C). CC, uninfected negative control cultures; VC, HIV-1 infected but untreated positive control cultures.
Figure 2B:
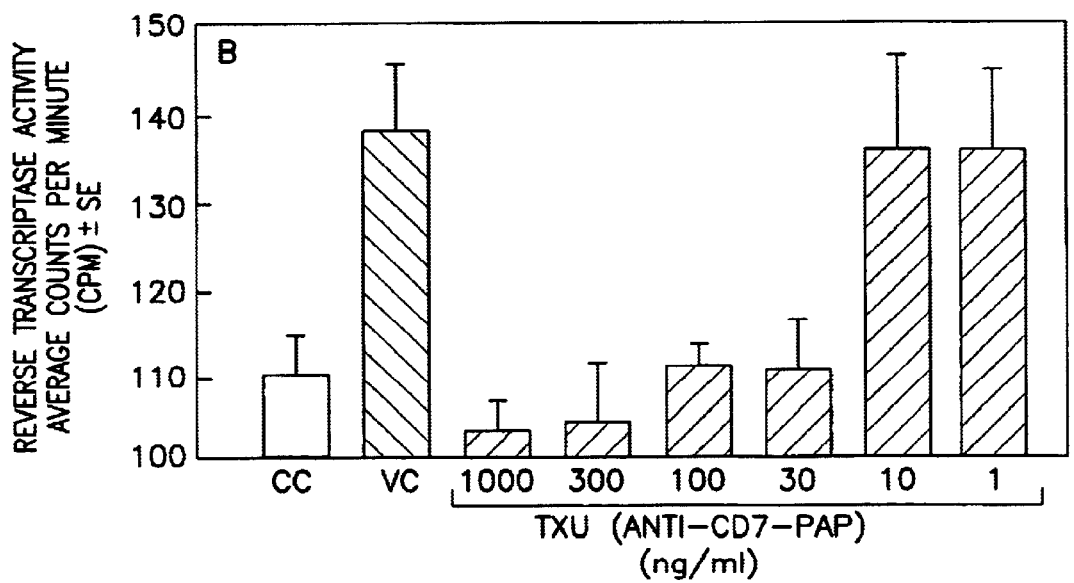
Figure 2C:
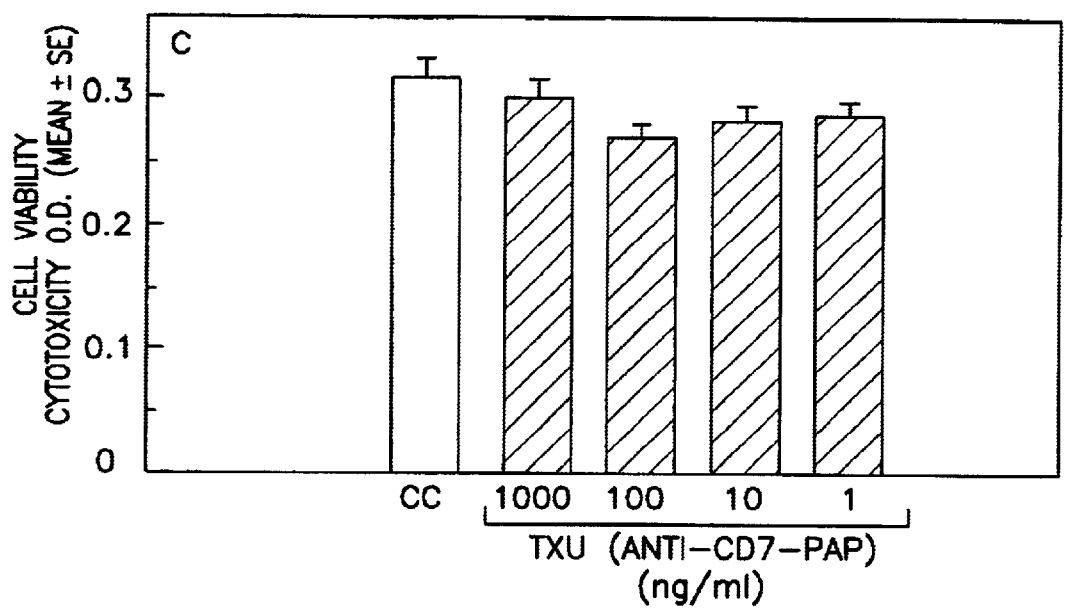
Figure 3A:
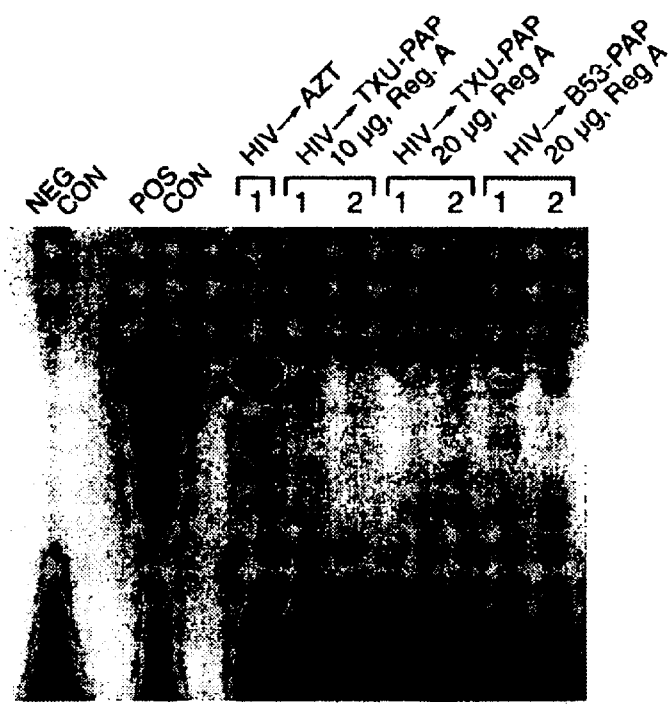
FIG. 3. In vivo anti-HIV-1 activity of TXU(anti-CD7)-PAP. Hu-PBL-SCID mice were inoculated with clinical HIV-1 isolates and PAP immunoconjugates were administered according to two schedules, Regimen A or Regimen B. Two weeks after infection with HIV-1, their peritoneal lavage cells (panels A and C) as well as spleen cells (panels B and D) were examined for evidence of infection by PCR amplification. Some mice were treated with AZT, added to their water at 1 mg/ml final concentration, resulting in an average consumption of 200 mg/kg/day of AZT. Controls included (1) the PCR reaction buffer without the genomic DNA (=NEG CON), (2) PCR reaction product of DNA from HIV-1 injected but unreconstituted SCID mice as well as from uninfected Hu-PBL-SCID mice as negative background controls, and (3) HIV-1 control plasmid DNA (POS CON) (Perkin-Elmer Cetus, Norwalk, Conn) as well as DNA from infected but untreated Hu-PBL SCID mice as positive DNA controls.
Figure 3B:
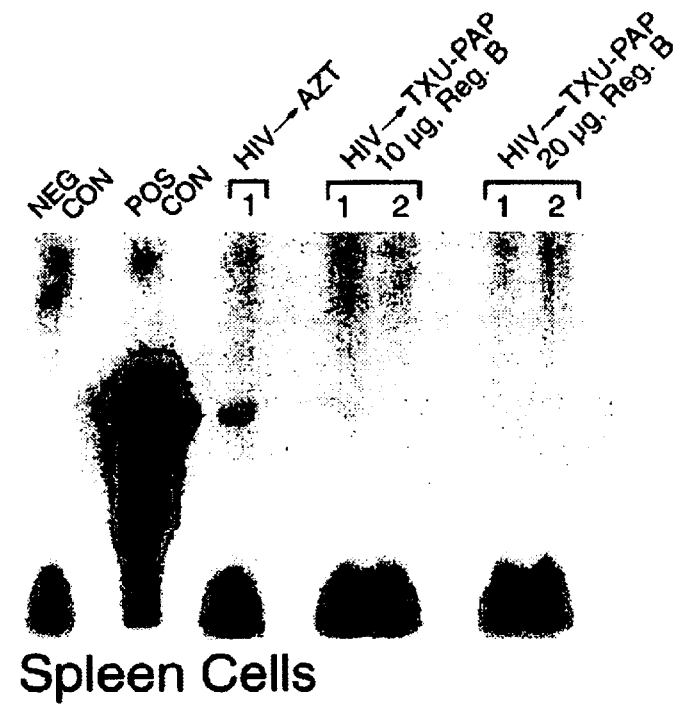
Figure 3C:
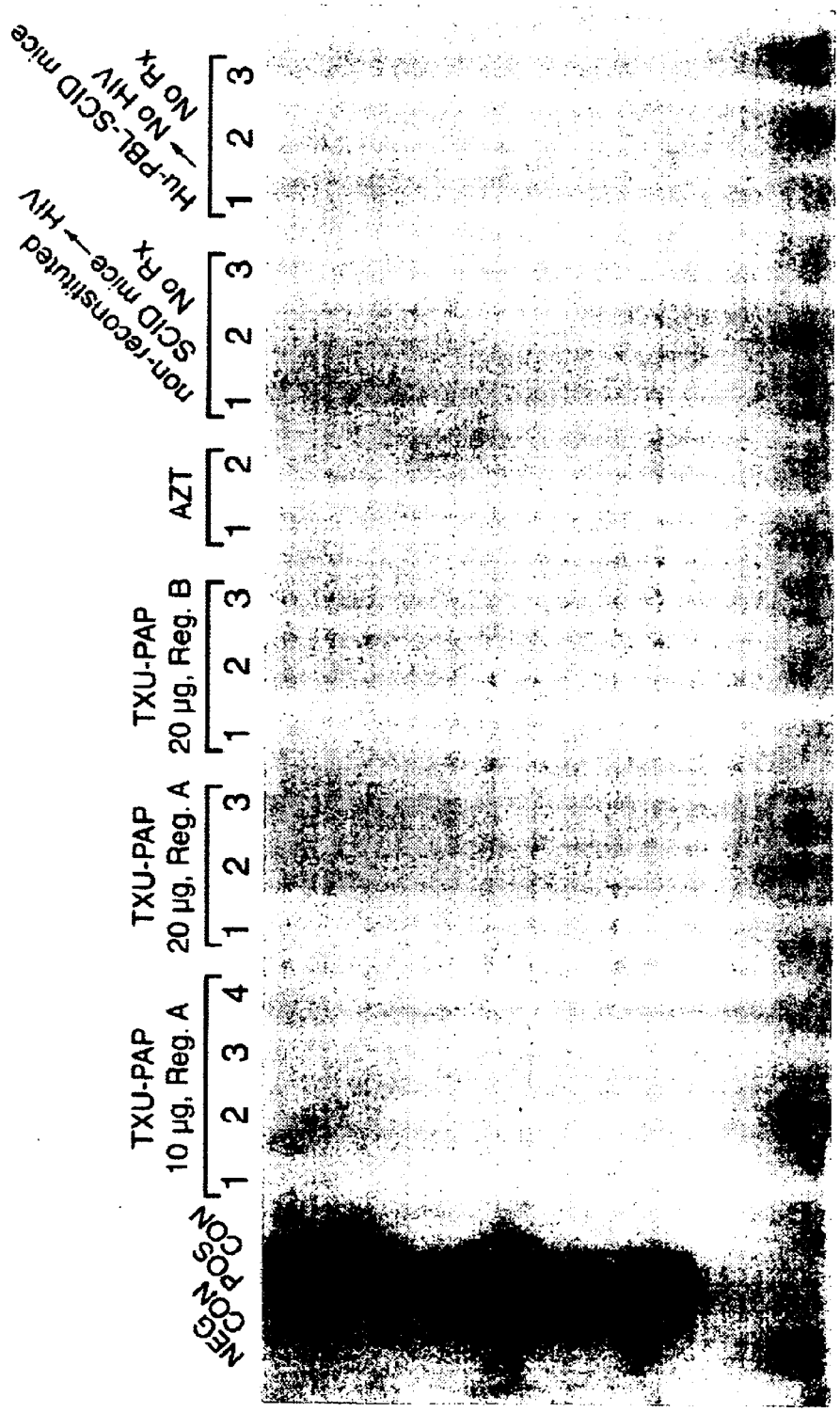
Figure 3D:
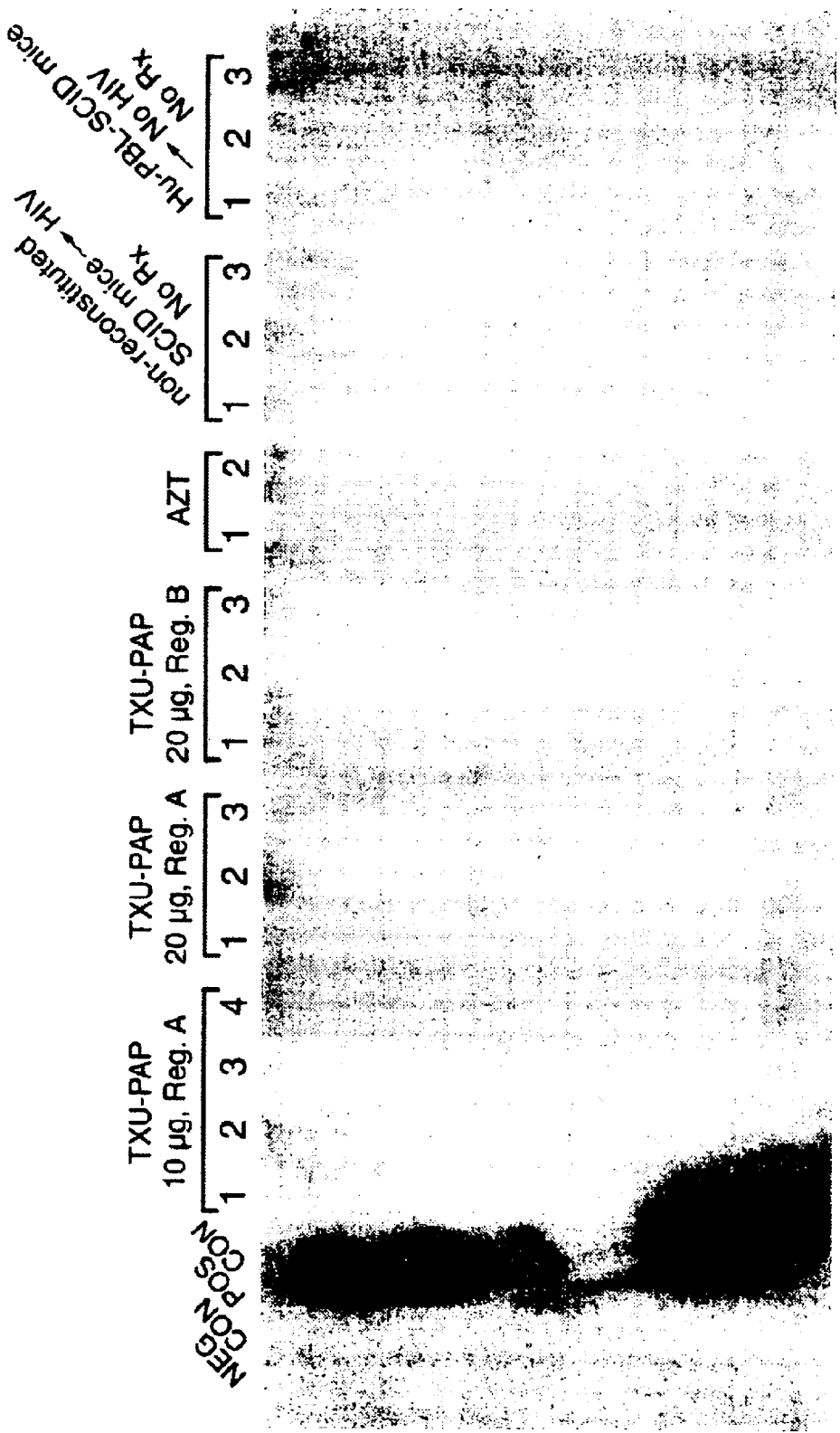

Overall, TXU(anti-CD7)-PAP was a slightly more potent anti-HIV-1 agent than B53(anti-CD4)-PAP. The anti-HIV-1 activity of TXU(anti-CD7)-PAP was highly reproducible and was not associated with significant cytotoxicity to T-cells (FIG. 2).

In Vivo Anti-HIV-1 Activity of B53(Anti-CD4AF and TXU(Anti-CD7)-PAP in a Surrogate SCID Mouse Model of Human AIDS. The in vivo anti-HIV-1 activity of B53(anti-CD4)-PAP and TXU(anti-CD7)PAP in a Hu-PBL-SCID mouse model of human AIDS was examined. As shown in Table 3, of the 23 Hu-PBL-SCID mice infected with HIV-1 and treated with PBS (a) 11 were analyzed by both HIV-culture and HIV-PCR and 10 were positive in both assays while one was only positive by PCR; (b) 6 were analyzed by HIV-culture only and all 6 were positive; and (c) 6 were analyzed by HIV-PCR only and all 6 were positive (ND=not determined). Similarly, 5 Hu-PBL-SCID mice infected with HIV-1 and treated with the B-cell directed control B43-PAP immunoconjugate were analyzed by HIV-PCR and all 5 tested positive, whereas no false positive results by HIV-culture or HIV-PCR were observed in any of the 17 control Hu-PBL-SCID mice that were not injected with HIV-1 (Table 3).

Figure 4A:
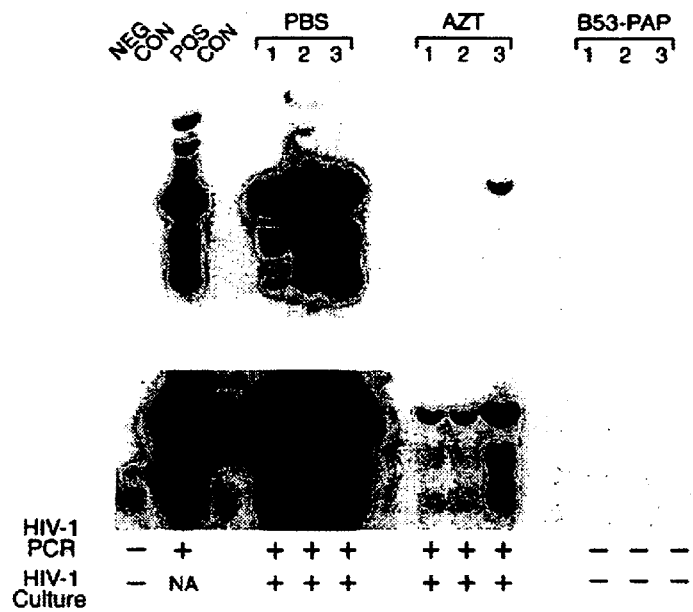
FIG. 4. In vivo anti-HIV-1 activity of B53(anti-CD4)-PAP. The antiviral activity of B53-PAP was examined in the Hu-PBL-SCID mouse model of human AIDS using HIV-PCR assays for evaluating the HIV-status of treated mice as well as a culture assay. AZT was added to their water at 1 mg/ml final concentration. Controls included (1) the PCR reaction buffer without the genomic DNA (=NEG CON), and (2) HIV-1 control plasmid DNA (POS CON) (Perkin-Elmer Cetus, Norwalk, Conn). N.D., not determined.
Figure 4B:
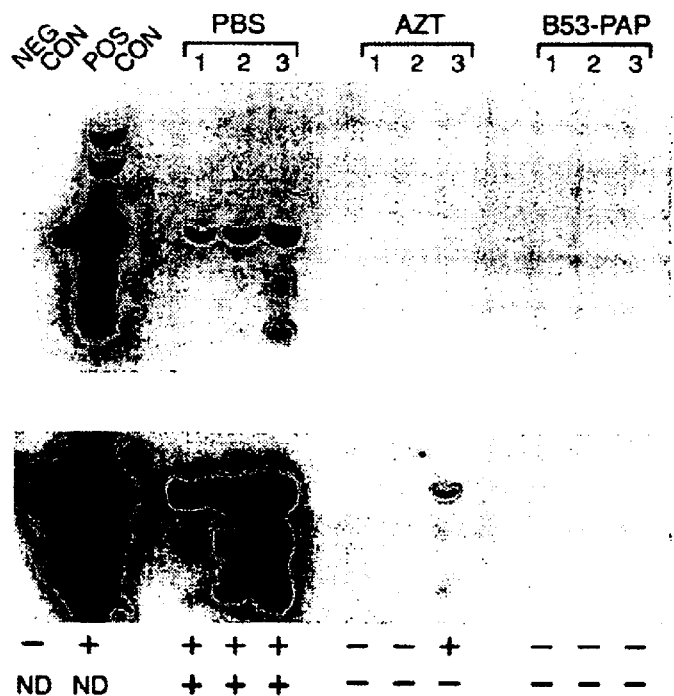

TXU(anti-CD7)-PAP elicited a more potent anti-HIV-1 activity in the Hu-PBL-SCID mouse model than B53(anti-CD4)-PAP. No PCR evidence of HIV-1 infection was found in any of the 20 Hu-PBL-SCID mice treated with 10 µg or 20 µg TXU(anti-CD7)-PAP administered according to the above-mentioned 14-day (Regimen A) or 5day (Regimen B) treatment schedules (FIG. 3, Table 3). By comparison, viral genomes were detected by PCR in all 4 Hu-PBL-SCID mice treated with B53(anti-CD4)-PAP at a total dose of 20 µg even though no virus was recovered by culture from any of these mice. At higher doses, B53(anti-CD4)PAP also elicited a potent anti-HIV-1 activity (FIG. 4). HIV-1 DNA was detected in only 3 of 18 Hu-PBL-SCID mice treated with B53(anti-CD4)-PAP at a total dose of 40 µg and none of the 11 mixed peritoneal lavage+splenocyte cultures from these mice were positive (FIG. 3, Table 3). Similarly, no culture or PCR evidence of HIV-1 infection was found in any of the 5 Hu-PBL-SCID mice treated with 60 µg B53(anti-CD4)PAP.

Importantly, $CD4^+CD7^+CD45^+gp120^-$T-cells were detected by multiparameter flow cytometry in the peritoneal lavage of Hu-PBL-SCID mice treated with 60 µg B53(anti-CD4)-PAP or 20 µg TXU(anti-CD7)-PAP and the presence of human DNA in spleen as well as peritoneal cavity of these

TABLE 3

Anti-HIV-1 Activity of TXU (anti-CD7)-PAP in Hu-PBL-SCID Mice

HIV-PCR and HIV-Culture Status of HIV-Infected Hu-PBL-SCID Mice

| Treatment | Total No. of SCID Mice | $PCR^+$ | $Cx^+$ | $PCR^+ Cx^+$ | $PCR^+ Cx^-$ | $PCR^+ Cx^{ND}$ | $PCR^- Cx^-$ | $PCR^{ND} Cx^+$ |
|---|---|---|---|---|---|---|---|---|
| PBS | 23 | 16/16 | 16/17 | 10/11 | 1/11 | 6/6 | 0/11 | 6/6 |
| TXU(anti-CD7)-PAP | | | | | | | | |
| 10 µg | 10 | 0/10 | ND | ND | ND | 0/10 | ND | ND |
| 20 µg | 10 | 0/10 | ND | ND | ND | 0/10 | ND | ND |
| B53(anti-CD4)-PAP | | | | | | | | |
| 10 µg | 5 | 5/5 | ND | ND | ND | 5/5 | ND | ND |
| 20 µg | 4 | 3/4 | 0/3 | 0/3 | 3/3 | 1/1 | 0/3 | ND |
| 40 µg | 18 | 3/18 | 0/11 | 0/11 | 2/11 | 1/7 | 9/11 | ND |
| 60 µg | 5 | 0/3 | 0/5 | 0/3 | 0/3 | ND | 3/3 | 0/2 |
| B43(anti-CD19)-PAP | | | | | | | | |
| 20 µg | 5 | 5/5 | ND | ND | ND | 5/5 | ND | ND |
| AZT | 10 | 4/10 | 4/8 | 4/8 | 4/8 | 0/2 | 0/8 | ND |
| Control Hu-PBL-SCID Mice (No HIV Infection, No treatment) | 17 | 0/9 | 0/16 | 0/8 | 0/8 | 0/1 | 8/8 | 0/8 |
| Control SCID Mice (No Hu-PBL, + HIV Infection, No treatment) | 3 | 0/3 | ND | ND | ND | 0/3 | ND | ND |

Hu-PBL-SCID mice were inoculated with clinical HIV-1 isolates in a Biosafety Level 3 containment facility. PAP immunoconjugates were administered intraperitoneally by injecting half of the total dose as an intraperitoneal bolus dose and delivering the remainder of the total dose over 2 weeks using Alzet micro-osmotic (Regimen A) pumps or by administering the total dose by daily intraperitoneal injections over a 5-day treatment period (Regimen B). Two weeks after infection with HIV-1, Hu-PBL-SCID mice were electively killed and their peritoneal lavage cells as well as spleen cells were examined for evidence of infection by an HIV-1 culture assay as well as by PCR amplification of a 115 bp DNA sequence in the gag region of the HIV-1 genome. In PBS-treated control Hu-PBL-SCID mice, HIV culture assays were performed using spleen cells (n=4), as well as a mixture of peritoneal lavage and spleen cells (n=12). HIV-PCR assays were performed on both spleen cells as well as peritoneal lavage cells except in 2 PBS treated Hu-PBL-SCID mice whose spleens were not examined by PCR.

Hu-PBL-SCID mice was confirmed by beta-globin gene PCR. Thus, the absence of HIV-1 in B53(anti-CD4)-PAP- or TXU(anti-CD7)-PAP-treated Hu-PBL-SCID mice was not caused by absence of human T-cells due to poor engraftment or PAP immunoconjugate-induced indiscriminate cytotoxicity. All mice treated with B53(anti-CD4)-PAP or TXU (anti-CD7)-PAP remained healthy throughout the test period. No overt signs of ill health or unusual responses were observed. In contrast to B53(anti-CD4)-PAP- or TXU (anti-CD7)-PAP-treated mice, only 3 of 10 Hu-PBL-SCID mice treated with AZT added to their water at 1 mg/ml final concentration, resulting in an average consumption of 200 mg/kg/day of AZT, tested HIV-1 negative. Of the remaining 7 mice, 4 were culture-positive and PCR positive, and 3 cases were culture-negative but PCR-positive (Table 3).

Multiflow cytometric analysis of surface antigens on lymphocytes obtained from the peritoneal cavities of untreated or ZDV-treated mice show the presence of gp120 on CD7 cells consistent with persistent HIV-1 infection, whereas CD7 cells from TXU-7-PAP treated mice are gp120 negative. The detection of human DNA and CD7 cells in TXU-7-PAP treated SCID mice provides evidence that the absence of HIV-1 in TXU-7-PAP treated Hu-PBL-SCID mice is not caused by absence of human CD7 cells due to poor engraftment or TXU-7-PAP cytotoxicity to CD7 cells. The results are clearly superior to those obtained with ZDV alone and indicate that TXU-7-PAP and ZDV can be safely combined.

Figure 5A:
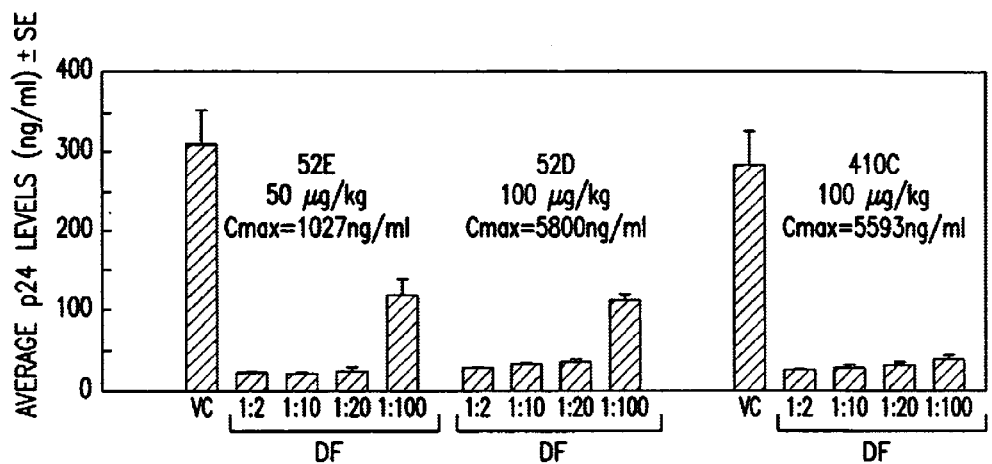
FIG. 5. In vitro anti-HIV-1 activity of plasma samples from TXU-PAP treated cynomolgus monkeys. The toxicity and pharmacokinetics of TXU-PAP in non-human primates was previously described (Waurzyniak et al., supra, a reference the disclosure of which is specifically incorporated by reference herein). Monkey 52E received a one-hour intravenous infusion of 50 μg/kg TXU-PAP, and monkeys 52D and 410C received a one-hour intravenous infusion of 100 μg/kg TXU-PAP one-hour prior to collection of the peripheral blood samples. The solid-phase ELISA based TXU-PAP levels were 1027 ng/mL in 52E plasma, 5800 ng/mL in 52D plasma, and 5593 ng/mL in 410C plasma. The in vitro effects of serially diluted plasma samples on HIV-1 replication were examined, using p24EIA and RT assays. The activity data is presented according to the plasma dilution factors (DF) used.
Figure 5B:
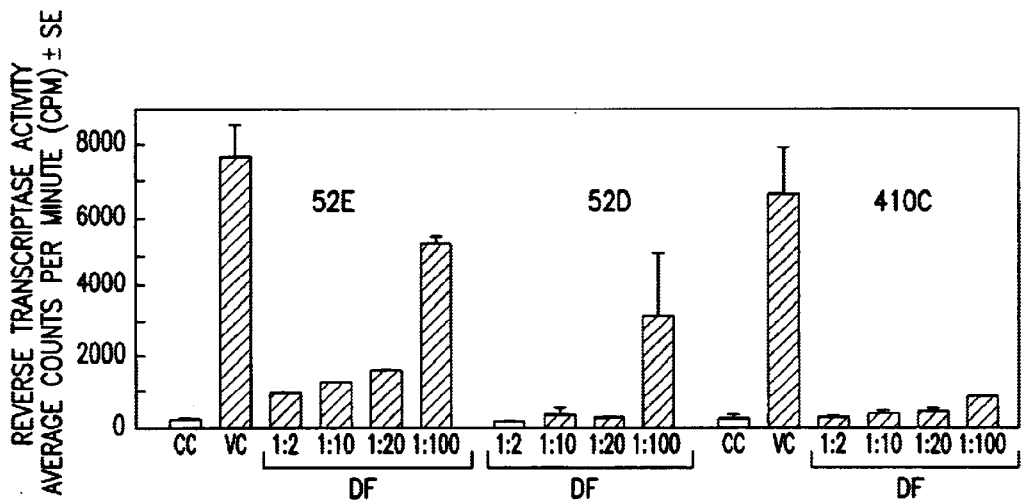

In Vitro Anti-HIV-1 Activity of Plasma Samples from TXU-PAP-treated Cynomolgus Monkeys. Monkeys treated with TXU-PAP experienced no significant side effects (Waurzyniak et al., supra). The TXU-PAP concentrations in the one-hour post-infusion plasma samples were 1027 ng/mL in 52E treated with 50 μg/kg TXU-PAP, 5800 ng/mL in 52D treated with 100 μg/kg TXU-PAP and 5593 ng/mL in 410C treated with 100 μg/kg TXU-PAP. As shown in FIG. 5, these plasma samples showed potent antiviral activity against HTLV$_{IIIB}$ in vitro even at a 1:100 dilution.

Discussion

The results described herein document the superior in vitro anti-HIV-1 activity of TXU-PAP in side by side comparison to AZT, d4T, unconjugated PAP, and B53-PAP, and an anti-CD4-PAP immunotoxin. Notably, TXU-PAP elicited potent anti-HIV activity in the Hu-PBL-SCID mouse model of human AIDS without any side effects and at dose levels that were very well tolerated by cynomolgus monkeys. Furthermore, plasma samples from TXU-PAP treated cynomolgus monkeys showed potent anti-HIV-1 activity in vitro.

Based on its potent anti-HIV-1 activity, the incorporation of this immunotoxin into clinical treatment protocols is expected to improve the prognosis for AIDS patients. A Phase I trial of such patients with TXU-PAP (BB-IND6985) has been initiated at a dose level of 0.001 mg/kg/day×5 days, which is 100-fold lower than the well-tolerated dose level of 0.1 mg/kg/day×5 days in cynomolgus monkeys and 25,000-fold lower than the $LD_{50}$ dose in BALB/c mice (i.e., 50 $\mu$g/mouse=2.5 mg/kg).

Thus, targeting PAP to uninfected or latently infected CD4+ cells using mAb against the normal antigens on CD4+ cells, such as the CD7 antigen, does not rely on the expression of HIV-1 envelope proteins on infected cells. This approach also avoids potential problems caused by envelope antigen heterogeneity among different HIV-1 isolates or the presence of plasma anti-envelope antibodies. It has been suggested that concomitant infections with other viruses such as CMV and HSV may induce HIV expression in latently infected CD4+ cells. The reported ability of PAP to inhibit the replication of many viruses including CMV and HSV is expected to therefore provide another unique advantage for the treatment of HIV-1 infections.

EXAMPLE 9

Treatment of HIV-Infected Chimpanzees With TXU-PAP

Three HIV-infected chimpanzees were treated with TXU-PAP. In this protocol TXU-PAP was administered intravenously as a single agent at a dose of 0.01 mg/kg/day for 10 consecutive days or as a single agent for 1 day at a dose of 0.02 mg/kg.

As indicated in Table 4, none of the chimpanzees experienced any significant side effects. In particular, no capillary leak syndrome was observed. Notably, the HIV viral load was reduced below PCR detectable levels in chimpanzee #1156 treated at the 0.02 mg/kg/dose level. The chimpanzee is currently alive at 100+ days with no evidence of any side effects. Therefore, TXU-PAP is active and safe.

TABLE 4

| Chimpanzee # | Sex | Dose mg/kg | Grade 2–4 Toxicity | Branched DNA Results (Copies/ml) According to Day on Study −26 | −15 | −7 | +6 | +11 | +29 | +57 | +88 |
|---|---|---|---|---|---|---|---|---|---|---|---|
| 881 | M | 0.01 | None | 1012 | 3855 | 4040 | N.D. | 4934 | 5296 | <500 | 2087 |
| 1150 | M | 0.01 | None | 1582 | 936 | 878 | 864 | 4575 | 4038 | <500 | 616 |
| 1156 | M | 0.02 | None | 1680 | 2722 | 1244 | <500 | N.D. | <500 | <500 | <500 |

N.D. - not done.

References

Aron, G. M. and Irvin, J. D. 1980. Inhibition of herpes simplex virus multiplication by the pokeweed antiviral protein, *Antimicrob. Ag. Chemother*. 17: 1032.

Chen, Z. C., Antoniw, J. F., White, R. F. and Lin, Q. 1992. Effect of pokeweed antiviral protein (PAP) on the infection of plant viruses, *Plant Pathol*. 40: 612.

Endo, Y., Tsurugi, K., and Lambert, J. M. 1988. The site of action of six different ribosome-inactivating proteins from plants on eukaryotic ribosomes: the RNA N-glycosidase activity of the proteins. *Biochem. Biophys. Res. Comm*. 150: 1032–1036.

Erice, A., Lieler, C. L., Meyers, D. E., Sannerund, K. J., Irvin, J. D., Balfour, H. H., and Uckun, F. M. 1993. Inhibition of zidovudine (AZT)-sensitive strains of human immunodeficiency virus type 1 by pokeweed antiviral protein targeted to CD4+ cells. *Antimicrob. Ag. Chemother*. 37:835.

Erice, A., Sannerud, K. J., Leske, V. L., Aeppli, D., and Balfour, H. H. 1992. Sensitive microculture method for isolation of human immunodeficiency virus type 1 from blood leukocytes. *J. Clin Microbiol*. 30:444–448.

Fauci, A. S., Schnittman, S. M., Poli, G., Koenig, S., and Pantaleo, G. 1991. Immunopathogenic mechanisms in human immunodeficiency virus (HIV) infection. *Annals of Internal Medicine* 114: 678–693.

Fauci, A. S. 1988. The human immunodeficiency virus: infectivity and mechanisms of pathogenesis. *Science* 239: 617–622.

Gehrz, R. C., Wilson, C., Eckhardt, J., Myers, D., Irvin, J. D., and Uckun, F. M. 1991. Treatment of human cytomegalovirus (HCMV) with novel antiviral immunoconjugates in Progress in Cytomegalovirus Research, M. P. Landin, ed. Elsevier Science Publishers BV, pp. 353–356.

Goudsmit, J., Lange, J. M. A, Paul, D. A., and Dawson, G. J. 1987. Antigenemia and antibody titers to core and envelope antigens in AIDS, AIDS-related complex, and subclinical human immunodeficiency virus infection. *J. Infect Diseases* 155: 558–560.

Hartley, M. R., Legname, G., Osborn, R., Chen, Z., and Lord, J. M. 1991. Single-chain ribosome inactivating proteins from plants depurinate *Escherichia coli* 23S ribosomal RNA. *FEBS Letters* 290: 65–68.

Ho, D. D., Pomerantz, R. J., and Kaplan, J. C. 1987. Pathogenesis of infection with human immunodeficiency virus. *NEJM* 317: 278–286.

Irvin, J. D. and Uckun, F. M. 1992. Pokeweed antiviral protein: Ribosome inactivation and therapeutic applications. *Pharmacology and Therapeutics* 55: 279–302.

Irvin, J. 1983. Pokeweed antiviral protein. *Pharmac. Ther.* 21: 371–387.

Jackson, J. B., Kwok, S. Y., Sninsky, J. J., Hopsicker, J. S., Sannerud, K. J., Rhame, F. S., Henry, K., Simpson, M., Balfour, and Jr H. H. 1990. Human immunodeficiency virus type 1 detected in all seropositive symptomatic and asymptomatic individuals. *J. Clin. Microbiol.* 28: 16–19.

Levy, J. A. and Shimabukuro, J. 1985. Recovery of AIDS-associated retroviruses from patients with AIDS or AIDS-related conditions and from clinically healthy individuals. *J. Infect. Diseases* 152: 734–738.

Mosier, D. E, Gulizia, R. Y, Baird, S. M, Wilson, D. B, Spector, D. H, and Spector, S. A. 1991. Human Immunodeficiency virus infection of human PBL-SCWD mice. *Science* 251:791–794.

Myers, D. E., Jun, X., Clementson, D., Donelson, R., Sicheneder, A., Hoffinan, N., Bell, K., Sarquis, M., Langlie, M., and Uckun, F. M. 1997. Large scale manufacturing of TXU(anti-CD7)-pokeweed antiviral protein (PAP) immunoconjugate for clinical trials. *Leukemia and Lymphoma*, in press.

Ou, C-Y, Kwok, S., Mitchell, S. W., Mackm D. H., Sninsky, J. J., Krebs, J. W., Feorino, P., Warefield, D., and Schochetman, G. 1988. DNA amplification for direct detection of HIV-1 in DNA of peripheral blood mononuclear cells. *Science* 239: 295–297.

Teltow, G. J., Irvin, J. D., and Aron, G. M. 1983. Inhibition of herpes simplex virus DNA synthesis by pokeweed antiviral protein, *Antimicrob. Ag. Chemother.* 23: 390.

Tomlinson, J. A., Walker, V. M., Flewett, T. H., and Barclay, G. R. 1974. The inhibition of infection of cucumber mosaic virus and influenza virus by extracts from Phytolacca americana. *J. Gen. Virol.* 22:225–232.

Ussery, M. A., Irvin, J. D., and Hardesty, B. 1977. Inhibition of poliovirus replication by a plant antiviral peptide. *Ann. N.Y. Acad. Sci.* 284: 431.

Waurzyniak, B., Schneider, E. A., Turner, N., Yanishevski, Y., Gunther, R., Chelstrom, L. M., Wendorf, H., Myers, D. E., Irvin, J. D., Messinger, Y., Ek, O., Zeren, T., Chandan-Langlie, M., Evans, W. E., and Uckun, F. M. 1997. In vivo toxicity, pharmacokinetics, and antileukemic activity of TXU (Anti-CD7)-pokeweed antiviral protein immunotoxin. *Clin Can. Res.* 3:881–890.

Zarling, J. M., Moran, P. A., Haffar, O., Sias, J., Richman, D. D., Spina, C. A., Myers, D. E., Kuebelbeck, V., Ledbetter, J. A., and Uckun, F. M. 1990. Inhibition of HIV replication by pokeweed antiviral protein targeted to CD4' cells by monoclonal antibodies. *Nature* 347: 92–95.

While only certain preferred embodiments of this invention have been shown and described by way of illustration, many modifications will occur to those skilled in the art and it is, therefore, desired that it be understood that this is intended herein to cover all such modifications that fall within the spirit and scope of this invention.

What is claimed is:

1. A method to enhance survival of a mammal having a neoplastic disease, comprising: parenterally administering to the mammal an effective amount of an immunotoxin comprising a TXU-7 antibody which is secreted by a hybridoma having ATCC No. HB-12260, or a biologically active fragment thereof, covalently linked to pokeweed antiviral protein, wherein the neoplastic cells express CD7, and wherein the neoplastic disease is T-cell leukemia, T-cell lymphoma or acute myeloid leukemia.

2. The method of claim 1 wherein the immunotoxin is administered in combination with a pharmaceutically acceptable liquid carrier.

3. The method of claim 2 wherein the liquid carrier comprises isotonic saline.

4. The method of claim 2 wherein the immunotoxin is administered intravenously.

5. The method of claim 1 wherein one or two molecules of pokeweed antiviral protein are covalently linked to each molecule of antibody.

6. The method of claim 1 further comprising the parenteral administration of an effective amount of an antineoplastic agent.

7. The method of claim 6 wherein the antineoplastic agent is a class I immunosuppressive drug or an antimetabolite.

8. The method of claim 7 wherein the antineoplastic agent is a class I immunosuppressive drug.

9. The method of claim 8 wherein the antineoplastic agent is cyclophosphamide.

10. The method of claim 11 wherein the antineoplastic agent is an antimetabolite.

11. The method of claim 10 wherein the antineoplastic agent is methotrexate, trimetrexate, 5-fluorouracil, cytarabine, mercaptopurine, thioguanine, 5-azacitidine or 2"-chlorodeoxyadenosine.

12. The method of claim 11 wherein the antineoplastic agent is cytarabine.

13. The method of claim 6 wherein the antineoplastic agent is combined with a pharmaceutically acceptable carrier.

14. The method of claim 6 wherein the antineoplastic agent is administered intravenously.

* * * * *

UNITED STATES PATENT AND TRADEMARK OFFICE
CERTIFICATE OF CORRECTION

PATENT NO. : 6,689,362 B2
DATED : February 10, 2004
INVENTOR(S) : Uckun

It is certified that error appears in the above-identified patent and that said Letters Patent is hereby corrected as shown below:

Title page,
Item [56], References Cited, OTHER PUBLICATIONS, "Allan, J.S.," reference, "Immunodeficency" and insert -- Immunodeficiency --, therefor; delete "Infectios" and insert -- Infections --, therefor.
"Lee, T.," reference, delete "Immunodefiency" and insert -- Immunodeficiency --, therefor; and after "et" delete ",".

Column 36,
Line 42, delete "claim 11" and insert -- claim 7 --, therefor.

Signed and Sealed this

Eighteenth Day of May, 2004

JON W. DUDAS
*Acting Director of the United States Patent and Trademark Office*

UNITED STATES PATENT AND TRADEMARK OFFICE
CERTIFICATE OF CORRECTION

PATENT NO. : 6,689,362 B1
DATED : February 10, 2004
INVENTOR(S) : Fatih M. Uckun It is certified that error appears in the above-identified patent and that said Letters Patent is hereby corrected as shown below:

Column 1,
Line 16, after "CA13539" add -- CA42111, RR08079 --.

Signed and Sealed this

Twenty-eighth Day of February, 2006

JON W. DUDAS
*Director of the United States Patent and Trademark Office*